US008466168B2

(12) United States Patent
Hubschwerlen et al.

(10) Patent No.: US 8,466,168 B2
(45) Date of Patent: Jun. 18, 2013

(54) TRICYCLIC ALKYLAMINOMETHYLOXAZOLIDINONE DERIVATIVES

(75) Inventors: Christian Hubschwerlen, Durmenach (FR); Georg Rueedi, Allschwil (CH); Jean-Philippe Surivet, Kembs (FR); Cornelia Zumbrunn-Acklin, Basel (CH)

(73) Assignee: Actellon Pharmaceuticals Ltd., Allschwil (CH)

( * ) Notice: Subject to any disclaimer, the term of this patent is extended or adjusted under 35 U.S.C. 154(b) by 320 days.

(21) Appl. No.: 13/057,650

(22) PCT Filed: Aug. 3, 2009

(86) PCT No.: PCT/IB2009/053356
§ 371 (c)(1),
(2), (4) Date: Feb. 4, 2011

(87) PCT Pub. No.: WO2010/015985
PCT Pub. Date: Feb. 11, 2010

(65) Prior Publication Data
US 2011/0136795 A1 Jun. 9, 2011

(30) Foreign Application Priority Data

Aug. 4, 2008 (WO) .................. PCT/IB2008/053112

(51) Int. Cl.
*C07D 471/04* (2006.01)
*C07D 491/04* (2006.01)

(52) U.S. Cl.
USPC ................ 514/292; 546/82; 546/89; 514/293

(58) Field of Classification Search
USPC ................................ 514/292, 293; 546/82, 89
See application file for complete search history.

(56) References Cited

U.S. PATENT DOCUMENTS

2004/0198755 A1 10/2004 Dartois et al.
2006/0205719 A1 9/2006 Hubschwerlen et al.

FOREIGN PATENT DOCUMENTS

| WO | WO 2004/058144 | 7/2004 |
| WO | WO 2006/032466 | 3/2006 |
| WO | WO 2007/081597 | 7/2007 |
| WO | WO 2007/122258 | 11/2007 |
| WO | WO 2007/044423 | 12/2007 |
| WO | WO 2008/003690 | 1/2008 |
| WO | WO 2008/026172 | 3/2008 |
| WO | WO 2008/126034 | 10/2008 |

OTHER PUBLICATIONS

Albert et al., Journal of Organic Chemistry, vol. 73, pp. 1093-1098 (2008).
Benz, Comprehensive Organic Synthesis, vol. 6, pp. 381-417 (1991).
Cha et al., Chemical Reviews, vol. 95, vol. 6, pp. 1761-1795 (1995).
Chang et al., Journal of Medicinal Chemistry, vol. 36, pp. 2558-2568 (1993).
Dess et al., Journal of Organic Chemistry, vol. 48, pp. 4155-4156 (1983).
Gerbino, Index for Remington, The Science and Practice of Pharmacy, 21$^{st}$ Edition (2005).
Gould, "Salt selection for basic drugs," *International Journal of Pharm.* 33: 201-217 (1986).
Greene et al., Protecting Groups in Organic Synthesis, 3$^{rd}$ Edition, pp. 494-653 (1999).
Greene et al., Protecting Groups in Organic Synthesis, 3$^{rd}$ Edition, pp. 17-245, particularly pp. 23-147, 133-139 and 142-143 (1999).
Johannes et al, Organic Letters, vol. 7, No. 18, pp. 3997-4000 (2005).

(Continued)

*Primary Examiner* — Rita Desai
(74) *Attorney, Agent, or Firm* — Hunton & Williams LLP

(57) ABSTRACT

The invention relates to antibacterial compounds of formula I

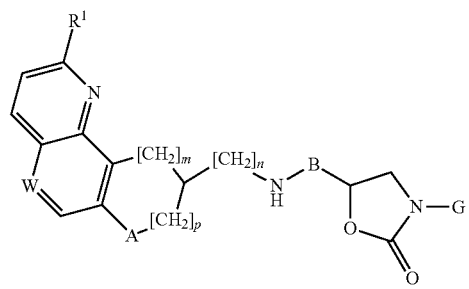

wherein
$R^1$ is alkoxy or halogen;
W is CH or N;
A is O or NH;
B is CO or $(CH_2)_q$;
G is a group having one of the three formulae below

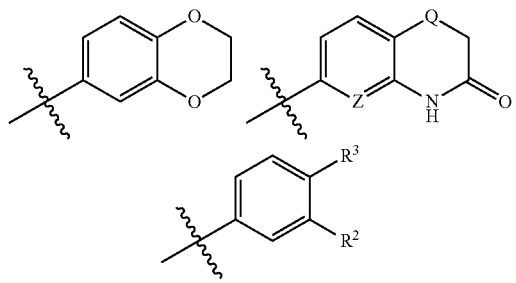

wherein Q represents O or S, Z represents CH or N, $R^2$ represents halogen and $R^3$ represents alkyl;
m is 0 or 1; and
n is 1 or 2;
p is 0 or 1, provided m and p are not each 0; and
q is 1 or 2;
and salts of such compounds.

15 Claims, No Drawings

OTHER PUBLICATIONS

Kolb et al., Chemical Reviews, vol. 94, No. 8, 2483-2547 (1994).
Kuwabe et al., American Chemical Society, vol. 123, pp. 12202-12206 (2001).
Larock, Comprehensive Organic Transformations, A guide to Functional Group Preparations 2nd Edition, Section Amines, pp. 779-784 (1999).
Larock, Comprehensive Organic Transformations. A guide to Functionnal Group Preparations; 2nd Edition, Wiley-VC; New York, Chichester, Weinheim, Brisbane, Singapore, Toronto, Section Nitriles, Carboxylic Acids and Derivatives, pp. 1646-1648 (1999).
Larock, R; Index of "Comprehensive Organic Transformations: A Guide to Functional Group Preparations," Second Edition, pp. 1941-1949 (1999).
Mitsunobu, Synthesis, vol. 1, pp. 1-28 (1981).
Sato et al., "One-Pot Reductive Amination of Aldehydes and Ketones with α-Picoline-Borane in Methanol, in Water, and in Neat Conditions," Tetrahedron, vol. 60, pp. 7899-7906 (2004).
Schmidt et al. J. Am. Chem. Soc. (2005), 127(32), 11426-11435.
Shafir et al., Journal of American Chemical Society, vol. 128, pp. 8742-8743 (2006).
Swern et al. Journal of Organic Chemistry, vol. 43, pp. 2480-2482 (1978).
Talbot et al., Clinical Infectious Diseases, vol. 42, pp. 657-668 (2006).
Vourloumis et al., Tetrahedron Letters, vol. 44, No. 14, pp. 2807-2811 (2003).
International Search Report for International Application PCT/IB2009/053356, mailed Nov. 5, 2009.
Written Opinion for International Application PCT/IB2009/053356, mailed Nov. 5, 2009.

TRICYCLIC ALKYLAMINOMETHYLOXAZOLIDINONE DERIVATIVES

CROSS-REFERENCE TO RELATED APPLICATIONS

This application is the national phase application of PCT/IB2009/053356, filed Aug. 3, 2009, which claims the benefit of PCT/IB2008/053112, filed Aug. 4, 2008, the contents of each are hereby incorporated by reference in their entirety.

FIELD OF THE INVENTION

The present invention concerns tricyclic alkylaminomethyloxazolidinone derivatives, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram-positive and Gram-negative aerobic and anaerobic bacteria and mycobacteria.

BACKGROUND OF THE INVENTION

The intensive use of antibiotics has exerted a selective evolutionary pressure on microorganisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:
- *S. aureus* is resistant to β-lactams, quinolones and now even to vancomycin;
- *S. pneumoniae* is becoming resistant to penicillin or quinolone antibiotics and even to new macrolides;
- *Enteroccocci* are quinolone and vancomycin resistant and β-lactam antibiotics are inefficacious against these strains;
- *Enterobacteriacea* are cephalosporin and quinolone resistant;
- *P. aeruginosa* are β-lactam and quinolone resistant.

Furthermore, the incidence of multi-drug-resistant Gram-negative strains such as *Enterobacteriacae* and *Pseudomonas aeruginosa*, is steadily increasing and new emerging organisms like *Acinetobacter* spp. or *Clostridium difficile*, which have been selected during therapy with the currently used antibiotics, are becoming a real problem in hospital settings. Therefore, there is a high medical need for new antibacterial agents which overcome multidrug-resistant Gram-negative bacilli such as *A. baumannii*, ESBL-producing *E. coli* and *Klebsiella* species and *Pseudomonas aeruginosa* (Clinical Infectious Diseases (2006), 42, 657-68).

In addition, microorganisms that are causing persistent infections are increasingly being recognized as causative agents or cofactors of severe chronic diseases like peptic ulcers or heart diseases.

DETAILED DESCRIPTION OF PREFERRED EMBODIMENTS

Certain antibacterial compounds comprising both a quinoline or naphthyridine moiety and an oxazolidinone group have been described in WO 2008/026172. In these compounds however, unlike the compounds of formula I described hereafter, the oxazolidinone is part of a spiro group and the quinoline or naphthyridine moiety is not part of a tricyclic group.

Various embodiments of the invention are presented hereafter.

i) The invention firstly relates to compounds of formula I

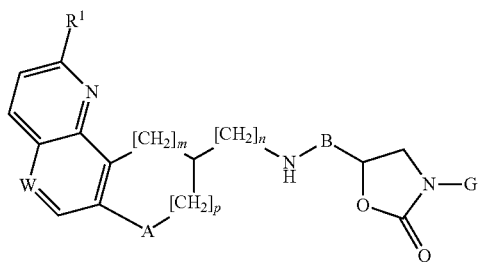

wherein
$R^1$ is alkoxy or halogen;
W is CH or N;
A is O or NH;
B is CO or $(CH_2)_q$;
G is a group having one of the three formulae below

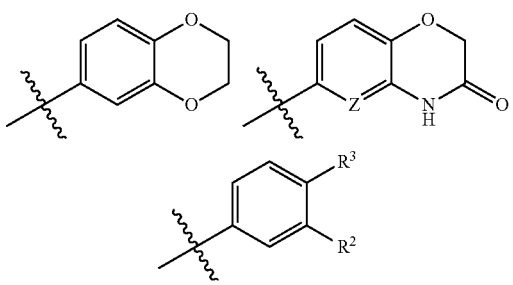

wherein Q represents O or S, Z represents CH or N (notably CH), $R^2$ represents halogen (notably fluorine) and $R^3$ represents alkyl;
m is 0 or 1;
n is 1 or 2;
p is 0 or 1, provided m and p are not each 0; and
q is 1 or 2;
and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a saturated straight or branched chain alkyl group containing from one to four carbon atoms. Representative examples of alkyl groups include methyl, ethyl, propyl, iso-propyl, n-butyl, iso-butyl, sec-butyl and tert-butyl. The term "$(C_1-C_x)$alkyl" (x being an integer) refers to a straight or branched chain alkyl group containing 1 to x carbon atoms.

The term "alkoxy", used alone or in combination, refers to a saturated straight or branched chain alkoxy group containing from one to four carbon atoms. Representative examples of alkoxy groups include methoxy, ethoxy, propoxy, iso-propoxy, n-butoxy, iso-butoxy, sec-butoxy and tert-butoxy. The term "$(C_1\text{-}C_x)$alkoxy" refers to a straight or branched chain alkoxy group containing 1 to x carbon atoms.

The term "halogen" refers to fluorine, chlorine, bromine or iodine, preferably to fluorine or chlorine.

In this text, a bond interrupted by a wavy line shows a point of attachment of the radical drawn to the rest of the molecule. For example, the radical drawn below

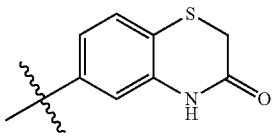 [SMILES: *c1ccc2c(c1)NC(=O)CS2]

is the 3-oxo-3,4-dihydro-2H-benzo[1,4]thiazin-6-yl group.

The compounds of formula I according to this invention may contain one or more stereogenic or asymmetric centers, such as one or more asymmetric carbon atoms. The compounds of formula I may thus be present as mixtures of stereoisomers or, preferably, as pure stereoisomers. Mixtures of stereoisomers may be separated in a manner known to a person skilled in the art.

Whenever the absolute stereochemistry indication "(R)" or "(S)" is omitted in the name of a compound although there is a corresponding asymmetric arbon atom, it is meant thereby that this compound name refers to either the (R)-configured compound or the (S)-configured compound.

The present invention also includes isotopically labelled, especially $^2$H (deuterium) labelled compounds of formula I, which compounds are identical to the compounds of formula I except that one or more atoms have each been replaced by an atom having the same atomic number but an atomic mass different from the atomic mass usually found in nature. Isotopically labelled, especially $^2$H (deuterium) labelled compounds of formula I and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one variant of the invention, the compounds of formula I are not isotopically labelled, or they are labelled only with one or more deuterium atoms. In a sub-variant, the compounds of formula I are not isotopically labelled at all. Isotopically labelled compounds of formula I may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

ii) The invention furthermore relates to compounds of formula I as defined in embodiment i) that are also compounds of formula $I_P$

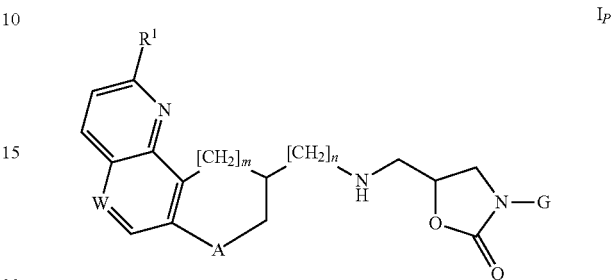

wherein $R^1$ is alkoxy or halogen;

W is CH or N;

A is O or NH;

G is a group having one of the two formulae below

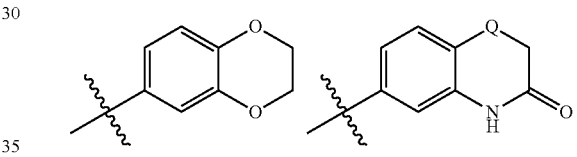

wherein Q represents O or S;

m is 0 or 1; and n is 1 or 2;

and to salts (in particular pharmaceutically acceptable salts) of compounds of formula $I_P$.

iii) In particular, the invention relates to compounds of formula I as defined in embodiment i) that are also compounds of formula $I_{CE}$

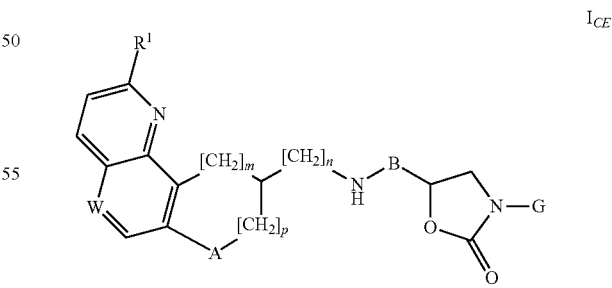

wherein $R^1$ is alkoxy (especially methoxy);

W is CH or N;

A is O or NH;

B is CO or $(CH_2)_q$;

G is a group of the formula

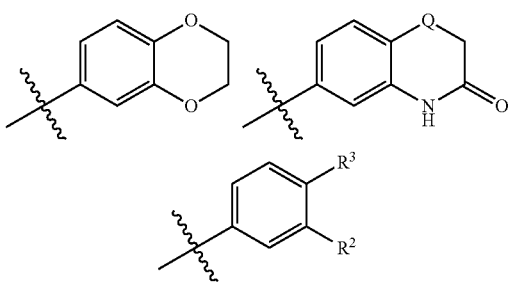

wherein Q represents O or S, $R^2$ represents halogen (notably fluorine) and $R^3$ represents alkyl (notably methyl);
m is 0 and n is 1 or 2 or m is 1 and n is 1;
p is 0 or 1, provided m and p are not each 0; and
q is 1 or 2;
and to salts (in particular pharmaceutically acceptable salts) of compounds of formula $I_{CE}$.

iv) The invention furthermore relates to compounds of formula $I_P$ as defined in embodiment ii) that are also compounds of formula $I_{CEP}$

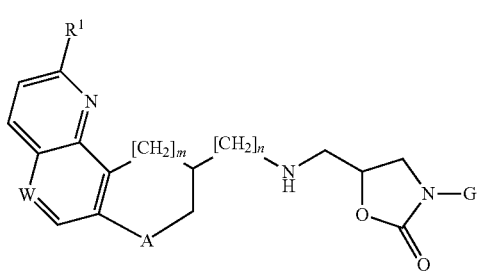

$I_{CEP}$ wherein
$R^1$ is alkoxy (especially methoxy);
W is CH or N;
A is O or NH;
G is a group of the formula

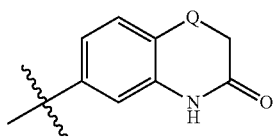

wherein Q represents O or S;
m is 0 and n is 1 or 2 or m is 1 and n is 1;
and to salts (in particular pharmaceutically acceptable salts) of compounds of formula $I_{CEP}$.

v) According to a preferred embodiment of this invention, the compounds of formula I as defined in one of embodiments i) to iv) above or their salts (among which the pharmaceutically acceptable salts will be preferred) will be such that $R^1$ is $(C_1-C_4)$alkoxy or fluorine (and preferably $(C_1-C_3)$alkoxy, in particular methoxy or ethoxy, especially methoxy) in the case of compounds of formula I as defined in embodiment i) or iii) or salts thereof, or such that $R^1$ is $(C_1-C_4)$alkoxy (and preferably $(C_1-C_3)$alkoxy, in particular methoxy or ethoxy, especially methoxy) in the case of compounds of formula I as defined in embodiment ii) or iv) or salts thereof vi) Another embodiment of this invention relates to the compounds of formula I as defined in one of embodiments i) to v) above or their salts (among which the pharmaceutically acceptable salts will be preferred) wherein W is CH.

vii) Yet another embodiment of this invention relates to the compounds of formula I as defined in one of embodiments i) to v) above or their salts (among which the pharmaceutically acceptable salts will be preferred) wherein W is N.

viii) According to one main variant of this invention, the compounds of formula I as defined in one of embodiments i) to vii) above or their salts (among which the pharmaceutically acceptable salts will be preferred) will be such that A is O (and notably such that A is O and p, if present, is 1).

ix) According to the other main variant of this invention, the compounds of formula I as defined in one of embodiments i) to vii) above or their salts (among which the pharmaceutically acceptable salts will be preferred) will be such that A is NH (and notably such that A is NH and each of m and p, if present, is 1).

x) According to one particular embodiment of this invention, the compounds of formula I as defined in one of embodiments i) to ix) above or their salts (among which the pharmaceutically acceptable salts will be preferred) will be such that p, if present, is 0 and m is 1.

xi) According to another particular embodiment of this invention, the compounds of formula I as defined in one of embodiments i) to ix) above or their salts (among which the pharmaceutically acceptable salts will be preferred) will be such that p, if present, is 1.

xii) One sub-embodiment of embodiment xi) relates to the compounds of formula I as defined in embodiment xi) above or their salts (among which the pharmaceutically acceptable salts will be preferred) wherein m is 0, n is 1 and B, if present, is $(CH_2)_q$, q being 1.

xiii) Another sub-embodiment of embodiment xi) relates to the compounds of formula I as defined in embodiment xi) above or their salts (among which the pharmaceutically acceptable salts will be preferred) wherein m is 0, n is 2 and B, if present, is $(CH_2)_q$, q being 1.

xiv) Yet another sub-embodiment of embodiment xi) relates to the compounds of formula I as defined in embodiment xi) above or their salts (among which the pharmaceutically acceptable salts will be preferred) wherein m is 1, n is 1 and B, if present, is $(CH_2)_q$, q being 1.

xv) Yet a further sub-embodiment of embodiment xi) relates to the compounds of formula I as defined in embodiment xi) above or their salts (among which the pharmaceutically acceptable salts will be preferred) wherein B, if present, is $(CH_2)_q$, q being 2 (and notably such that m is 0, n is 2 and B, if present, is $(CH_2)_q$, q being 2).

xvi) According to one main embodiment of this invention, the compounds of formula I as defined in embodiment i) or iii) above or in any of embodiments v) to xi) taken together with embodiment i) or iii) above, or their salts (among which the pharmaceutically acceptable salts will be preferred), will be such that B is CO.

xvii) According to another main embodiment of this invention, the compounds of formula I as defined in one of embodiments i) to xv) above or their salts (among which the pharmaceutically acceptable salts will be preferred) will be such that B, if present, is $(CH_2)_q$.

xviii) One sub-embodiment of embodiment xvii) relates to the compounds of formula I as defined in embodiment xvii) above or their salts (among which the pharmaceutically acceptable salts will be preferred) wherein q is 1 (and notably such that n is 1 and q is 1).

xix) The other sub-embodiment of embodiment xvii) relates to the compounds of formula I as defined in embodiment xvii) above or their salts (among which the pharmaceutically acceptable salts will be preferred) wherein q is 2.

xx) Preferably, the compounds of formula I as defined in embodiments i) to xix) above or their salts (among which the pharmaceutically acceptable salts will be preferred) will be such that G represents a group of the formula

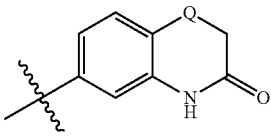

wherein Q represents O or S.

xxi) As an alternative, the compounds of formula I as defined in embodiments i) to xix) above or their salts (among which the pharmaceutically acceptable salts will be preferred) will be such that G represents a group of the formula

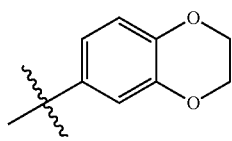 [SMILES: *c1ccc2c(c1)OCCO2]

xxii) As a further alternative, the compounds of formula I as defined in embodiment i) or iii) above or in any of embodiments v) to xix) taken together with embodiment i) or iii) above, or their salts (among which the pharmaceutically acceptable salts will be preferred), will be such that G represents a group of the formula

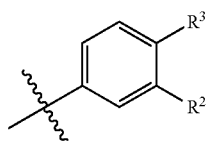

wherein $R^2$ represents halogen (preferably fluorine) and $R^3$ represents alkyl (preferably methyl).

xxiii) Preferably also, the compounds of formula I as defined in embodiments i) to xxii) above or their salts (among which the pharmaceutically acceptable salts will be preferred) will be such that their stereochemistry is as drawn below

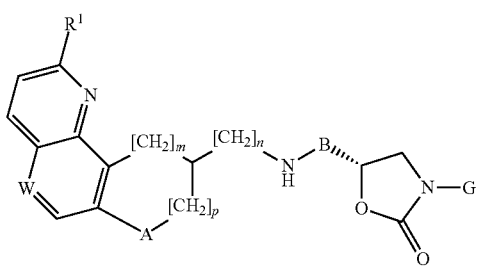

or, in the particular cases of compounds of formula $I_P$ or $I_{CEP}$,

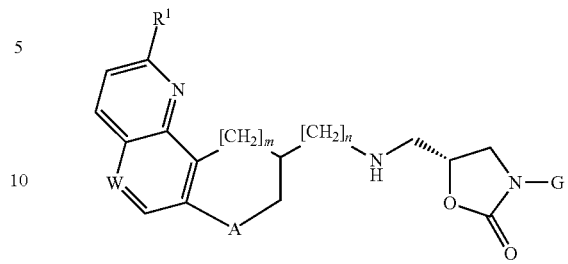

xxiv) Particularly preferred are the following compounds of formula I as defined in one of embodiments i) to iv):

6-((R)-5-{[(6-methoxy-3,4-dihydro-2H-1-oxa-5-aza-phenanthren-3-ylmethyl)-amino]-methyl}-2-oxo-oxazolidin-3-yl)-4H-benzo[1,4]thiazin-3-one;
6-((R)-5-{[(6-methoxy-3,4-dihydro-2H-1-oxa-5-aza-phenanthren-3-ylmethyl)-amino]-methyl}-2-oxo-oxazolidin-3-yl)-4H-benzo[1,4]oxazin-3-one;
6-((R)-5-{[(6-methoxy-3,4-dihydro-2H-1-oxa-5,9-diaza-phenanthren-3-ylmethyl)-amino]-methyl}-2-oxo-oxazolidin-3-yl)-4H-benzo[1,4]oxazin-3-one;
6-((R)-5-{[(6-methoxy-3,4-dihydro-2H-1-oxa-5,9-diaza-phenanthren-3-ylmethyl)-amino]-methyl}-2-oxo-oxazolidin-3-yl)-4H-benzo[1,4]thiazin-3-one;
6-((R)-5-{[(6-methoxy-1,2,3,4-tetrahydro-1,5,9-triaza-phenanthren-3-ylmethyl)-amino]-methyl}-2-oxo-oxazolidin-3-yl)-4H-benzo[1,4]thiazin-3-one;
6-((R)-5-{[2-(2-methoxy-8,9-dihydro-furo[2,3-h]quinolin-9-yl)-ethylamino]-methyl}-2-oxo-oxazolidin-3-yl)-4H-benzo[1,4]thiazin-3-one;
6-((R)-5-{[2-(2-methoxy-8,9-dihydro-furo[2,3-h]quinolin-9-yl)-ethylamino]-methyl}-2-oxo-oxazolidin-3-yl)-4H-benzo[1,4]oxazin-3-one,
6-((R)-5-{[(2-methoxy-8,9-dihydro-furo[2,3-h]quinolin-9-ylmethyl)-amino]-methyl}-2-oxo-oxazolidin-3-yl)-4H-benzo[1,4]thiazin-3-one;

as well as the salts (in particular the pharmaceutically acceptable salts) thereof.

xxv) A further object of this invention thus relates to the following compounds of formula I as defined in one of embodiments i) to iv):

6-((R)-5-{[((R)-6-methoxy-3,4-dihydro-2H-1-oxa-5-aza-phenanthren-3-ylmethyl)-amino]-methyl}-2-oxo-oxazolidin-3-yl)-4H-benzo[1,4]thiazin-3-one;
6-((R)-5-{[((S)-6-methoxy-3,4-dihydro-2H-1-oxa-5-aza-phenanthren-3-ylmethyl)-amino]-methyl}-2-oxo-oxazolidin-3-yl)-4H-benzo[1,4]thiazin-3-one;
6-((R)-5-{[((R)-6-methoxy-3,4-dihydro-2H-1-oxa-5-aza-phenanthren-3-ylmethyl)-amino]-methyl}-2-oxo-oxazolidin-3-yl)-4H-benzo[1,4]oxazin-3-one;
6-((R)-5-{[((S)-6-methoxy-3,4-dihydro-2H-1-oxa-5-aza-phenanthren-3-ylmethyl)-amino]-methyl}-2-oxo-oxazolidin-3-yl)-4H-benzo[1,4]oxazin-3-one;
6-((R)-5-{[((R)-6-methoxy-3,4-dihydro-2H-1-oxa-5,9-diaza-phenanthren-3-ylmethyl)-amino]-methyl}-2-oxo-oxazolidin-3-yl)-4H-benzo[1,4]oxazin-3-one;
6-((R)-5-{[((S)-6-methoxy-3,4-dihydro-2H-1-oxa-5,9-diaza-phenanthren-3-ylmethyl)-amino]-methyl}-2-oxo-oxazolidin-3-yl)-4H-benzo[1,4]oxazin-3-one;
6-((R)-5-{[((R)-6-methoxy-3,4-dihydro-2H-1-oxa-5,9-diaza-phenanthren-3-ylmethyl)-amino]-methyl}-2-oxo-oxazolidin-3-yl)-4H-benzo[1,4]thiazin-3-one;
6-((R)-5-{[((S)-6-methoxy-3,4-dihydro-2H-1-oxa-5,9-diaza-phenanthren-3-ylmethyl)-amino]-methyl}-2-oxo-oxazolidin-3-yl)-4H-benzo[1,4]thiazin-3-one;

6-((R)-5-{[((R)-6-methoxy-1,2,3,4-tetrahydro-1,5,9-triaza-phenanthren-3-ylmethyl)-amino]-methyl}-2-oxo-oxazo-lidin-3-yl)-4H-benzo[1,4]thiazin-3-one;

6-((R)-5-{[((S)-6-methoxy-1,2,3,4-tetrahydro-1,5,9-triaza-phenanthren-3-ylmethyl)-amino]-methyl}-2-oxo-oxazo-lidin-3-yl)-4H-benzo[1,4]thiazin-3-one;

6-((R)-5-{[2-((R)-2-methoxy-8,9-dihydro-furo[2,3-h]quinolin-9-yl)-ethylamino]-methyl}-2-oxo-oxazolidin-3-yl)-4H-benzo[1,4]thiazin-3-one;

6-((R)-5-{[2-((S)-2-methoxy-8,9-dihydro-furo[2,3-h]quinolin-9-yl)-ethylamino]-methyl}-2-oxo-oxazolidin-3-yl)-4H-benzo[1,4]thiazin-3-one;

6-((R)-5-{[2-((R)-2-methoxy-8,9-dihydro-furo[2,3-h]quinolin-9-yl)-ethylamino]-methyl}-2-oxo-oxazolidin-3-yl)-4H-benzo[1,4]oxazin3-one, 6-((R)-5-{[2-((S)-2-methoxy-8,9-dihydro-furo[2,3-h]quinolin-9-yl)-ethylamino]-methyl}-2-oxo-oxazolidin-3-yl)-4H-benzo[1,4]oxazin-3-one, 6-((R)-5-{[((R)-2-methoxy-8,9-dihydro-furo[2,3-h]quinolin-9-ylmethyl)-amino]-methyl}-2-oxo-oxazolidin-3-yl)-4H-benzo[1,4]thiazin-3-one;

6-((R)-5-{[((S)-2-methoxy-8,9-dihydro-furo[2,3-h]quinolin-9-ylmethyl)-amino]-methyl}-2-oxo-oxazolidin-3-yl)-4H-benzo[1,4]thiazin-3-one;

as well as to the salts (in particular the pharmaceutically acceptable salts) thereof.

xxvi) Further particularly preferred compounds of formula I as defined in embodiment i) or iii) are the following compounds:

6-((R)-5-{[2-(8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]thiazin-3-one;

6-((R)-5-{[2-(8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]oxazin-3-one;

(R)-3-(3-fluoro-4-methyl-phenyl)-5-{[2-(8-methoxy-1,2-dihydro-3-oxa-5,9-diaza-cyclopenta[a]naphthalen-1-yl)-ethylamino]-methyl}-oxazolidin-2-one;

6-((S)-5-{[2-(8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]thiazin-3-one;

6-((R)-5-{2-[2-(8-methoxy-1,2-dihydro-3-oxa-5,9-diaza-cyclopenta[a]naphthalen-ethylamino]-ethyl}-2-oxo-oxazolidin-3-yl)-4H-benzo[1,4]thiazin-3-one;

6-((R)-5-{2-[(8-methoxy-1,2-dihydro-3-oxa-5,9-diaza-cyclopenta[a]naphthalen-1-ylmethyl)-amino]-ethyl}-2-oxo-oxazolidin-3-yl)-4H-benzo[1,4]thiazin-3-one;

6-((S)-5-{2-[(8-methoxy-1,2-dihydro-3-oxa-5,9-diaza-cyclopenta[a]naphthalen-1-ylmethyl)-amino]-ethyl}-2-oxo-oxazolidin-3-yl)-4H-benzo[1,4]thiazin-3-one;

(S)-3-(2,3-dihydro-benzo[1,4]dioxin-6-yl)-2-oxo-oxazolidine-5-carboxylic acid [2-(8-methoxy-1,2-dihydro-3-oxa-5,9-diaza-cyclopenta[a]naphthalen-1-yl)-ethyl]-amide;

6-((R)-5-{[(8-methoxy-1,2-dihydro-3-oxa-5,9-diaza-cyclopenta[a]naphthalen-2-ylmethyl)-amino]-methyl}-2-oxo-oxazolidin-3-yl)-4H-benzo[1,4]thiazin-3-one;

6-((R)-5-{2-[(8-methoxy-1,2-dihydro-3-oxa-5,9-diaza-cyclopenta[a]naphthalen-2-ylmethyl)-amino]-ethyl}-2-oxo-oxazolidin-3-yl)-4H-benzo[1,4]oxazin-3-one;

6-((R)-5-{2-[(8-methoxy-1,2-dihydro-3-oxa-5,9-diaza-cyclopenta[a]naphthalen-2-ylmethyl)-amino]-ethyl}-2-oxo-oxazolidin-3-yl)-4H-benzo[1,4]thiazin-3-one;

3-(2,3-dihydro-benzo[1,4]dioxin-6-yl)-5-{[2-((R)-8-methoxy-1,2-dihydro-3-oxa-5,9-diaza-cyclopenta[a]naphthalen-1-yl)-ethylamino]-methyl}-oxazolidin-2-one;

as well as the salts (in particular the pharmaceutically acceptable salts) thereof.

xxvii) A further object of this invention thus relates to the following compounds of formula I as defined in embodiment i) or iii):

6-((R)-5-{[2-((R)-8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]thiazin-3-one;

6-((R)-5-{[2-((S)-8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]thiazin-3-one;

6-((R)-5-{[2-((R)-8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]oxazin-3-one;

6-((R)-5-{[2-((S)-8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]oxazin-3-one;

(R)-3-(3-fluoro-4-methyl-phenyl)-5-{[2-((R)-8-methoxy-1,2-dihydro-3-oxa-5,9-diaza-cyclopenta[a]naphthalen-1-yl)-ethylamino]-methyl}-oxazolidin-2-one;

(R)-3-(3-fluoro-4-methyl-phenyl)-5-{[2-((S)-8-methoxy-1,2-dihydro-3-oxa-5,9-diaza-cyclopenta[a]naphthalen-1-yl)-ethylamino]-methyl}-oxazolidin-2-one;

6-((S)-5-{[2-((R)-8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]thiazin-3-one;

6-((S)-5-{[2-((S)-8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]thiazin-3-one;

6-((R)-5-{2-[2-((R)-8-methoxy-1,2-dihydro-3-oxa-5,9-diaza-cyclopenta[a]naphthalen-1-yl)-ethylamino]-ethyl}-2-oxo-oxazolidin-3-yl)-4H-benzo[1,4]thiazin-3-one;

6-((R)-5-{2-[2-((S)-8-methoxy-1,2-dihydro-3-oxa-5,9-diaza-cyclopenta[a]naphthalen-1-yl)-ethylamino]-ethyl}-2-oxo-oxazolidin-3-yl)-4H-benzo[1,4]thiazin-3-one;

6-((R)-5-{2-[((R)-8-methoxy-1,2-dihydro-3-oxa-5,9-diaza-cyclopenta[a]naphthalen-1-ylmethyl)-amino]-ethyl}-2-oxo-oxazolidin-3-yl)-4H-benzo[1,4]thiazin-3-one;

6-((R)-5-{2-[((S)-8-methoxy-1,2-dihydro-3-oxa-5,9-diaza-cyclopenta[a]naphthalen-1-ylmethyl)-amino]-ethyl}-2-oxo-oxazolidin-3-yl)-4H-benzo[1,4]thiazin-3-one;

6-((S)-5-{2-[((R)-8-methoxy-1,2-dihydro-3-oxa-5,9-diaza-cyclopenta[a]naphthalen-1-ylmethyl)-amino]-ethyl}-2-oxo-oxazolidin-3-yl)-4H-benzo[1,4]thiazin-3-one;

6-((S)-5-{2-[((S)-8-methoxy-1,2-dihydro-3-oxa-5,9-diaza-cyclopenta[a]naphthalen-1-ylmethyl)-amino]-ethyl}-2-oxo-oxazolidin-3-yl)-4H-benzo[1,4]thiazin-3-one;

(S)-3-(2,3-dihydro-benzo[1,4]dioxin-6-yl)-2-oxo-oxazolidine-5-carboxylic acid [2-((R)-8-methoxy-1,2-dihydro-3-oxa-5,9-diaza-cyclopenta[a]naphthalen-1-yl)-ethyl]-amide;

(S)-3-(2,3-dihydro-benzo[1,4]dioxin-6-yl)-2-oxo-oxazolidine-5-carboxylic acid [2-((S)-8-methoxy-1,2-dihydro-3-oxa-5,9-diaza-cyclopenta[a]naphthalen-1-yl)-ethyl]-amide;

6-((R)-5-{[((R)-8-methoxy-1,2-dihydro-3-oxa-5,9-diaza-cyclopenta[a]naphthalen-2-ylmethyl)-amino]-methyl}-2-oxo-oxazolidin-3-yl)-4H-benzo[1,4]thiazin-3-one;

6-((R)-5-{[((S)-8-methoxy-1,2-dihydro-3-oxa-5,9-diaza-cyclopenta[a]naphthalen-2-ylmethyl)-amino]-methyl}-2-oxo-oxazolidin-3-yl)-4H-benzo[1,4]thiazin-3-one;

6-((R)-5-{2-[((R)-8-methoxy-1,2-dihydro-3-oxa-5,9-diaza-cyclopenta[a]naphthalen-2-ylmethyl)-amino]-ethyl}-2-oxo-oxazolidin-3-yl)-4H-benzo[1,4]oxazin-3-one;

6-((R)-5-{2-[((S)-8-methoxy-1,2-dihydro-3-oxa-5,9-diaza-cyclopenta[a]naphthalen-2-ylmethyl)-amino]-ethyl}-2-oxo-oxazolidin-3-yl)-4H-benzo[1,4]oxazin-3-one;

6-((R)-5-{2-[((R)-8-methoxy-1,2-dihydro-3-oxa-5,9-diaza-cyclopenta[a]naphthalen-2-ylmethyl)-amino]-ethyl}-2-oxo-oxazolidin-3-yl)-4H-benzo[1,4]thiazin-3-one;

6-((R)-5-{2-[((S)-8-methoxy-1,2-dihydro-3-oxa-5,9-diaza-cyclopenta[a]naphthalen-2-ylmethyl)-amino]-ethyl}-2-oxo-oxazolidin-3-yl)-4H-benzo[1,4]thiazin-3-one;

(R)-3-(2,3-dihydro-benzo[1,4]dioxin-6-yl)-5-{[2-((R)-8-methoxy-1,2-dihydro3-oxa-5,9-diaza-cyclopenta[a]naphthalen-1-yl)-ethylamino]-methyl}-oxazolidin-2-one;

(S)-3-(2,3-dihydro-benzo[1,4]dioxin-6-yl)-5-{[2-((R)-8-methoxy-1,2-dihydro-3-oxa-5,9-diaza-cyclopenta[a]naphthalen-1-yl)-ethylamino]-methyl}-oxazolidin-2-one;

as well as to the salts (in particular the pharmaceutically acceptable salts) thereof.

xxxviii) The invention further relates to the compounds of formula I as defined in embodiment i) or iii) which are selected from the group consisting of the compounds listed in embodiment xxxiv) and the compounds listed in embodiment xxxvi), as well as to the salts (in particular the pharmaceutically acceptable salts) of such compounds.

xxxix) The invention moreover relates to the compounds of formula I as defined in embodiment i) or iii) which are selected from the group consisting of the compounds listed in embodiment xxxv) and the compounds listed in embodiment xxxvii), as well as to the salts (in particular the pharmaceutically acceptable salts) of such compounds.

The compounds of formula I according to the invention, i.e. according to one of embodiments i) to xxxix), are suitable for the use as chemotherapeutic active compounds in human and veterinary medicine and as substances for preserving inorganic and organic materials in particular all types of organic materials for example polymers, lubricants, paints, fibres, leather, paper and wood.

The compounds of formula I according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. cassehflavus, S. epidermidis, S. haemolyticus,* or *Peptostreptococcus* spp.; pharyngitis, rheumatic fever, and glomerulonephritis related to infection by *Streptococcus pyogenes*, Groups C and G streptococci, *Corynebacterium diphtherias*, or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; infections caused by *Mycobacterium tuberculosis, M. leprae, M. paratuberculosis, M. kansasii,* or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae.*

The compounds of formula I according to the present invention are further useful for the preparation of a medicament for the treatment of infections that are mediated by bacteria such as *E. coli, Klebsiella pneumoniae* and other Enterobacteriaceae, *Acinetobacter* spp. including *Acinetobacter baumanii, Stenothrophomonas maltophilia, Neisseria meningitidis, Bacillus cereus, Bacillus anthracis, Clostridium difficile, Corynebacterium* spp., *Propionibacterium acnes* and bacteroide spp.

The compounds of formula I according to the present invention are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

The compounds of fomula I according to this invention, or the pharmaceutically acceptable salt thereof, may be used for the preparation of a medicament, and are suitable, for the prevention or treatment (and notably for the treatment) of a bacterial infection.

One aspect of this invention therefore relates to the use of a compound of formula I according to one of embodiments i) to xxxix), or of a pharmaceutically acceptable salt thereof, for the manufacture of a medicament for the prevention or treatment (and notably for the treatment) of a bacterial infection. Another aspect of this invention relates to a compound of formula I according to one of embodiments i) to xxxix), or of a pharmaceutically acceptable salt thereof, for the prevention or treatment (and notably for the treatment) of a bacterial infection.

Accordingly, the compounds of formula I according to one of embodiments i) to xxxix), or the pharmaceutically acceptable salts thereof, may be used for the preparation of a medicament, and are suitable, for the prevention or treatment (and notably for the treatment) of a bacterial infection selected from the group consisting of respiratory tract infections, otitis media, meningitis, skin and soft tissue infections (whether complicated or uncomplicated), pneumonia (including hospital acquired pneumonia), bacteremia, endocarditis, intraabdominal infections, gastrointestinal infections, *Clostridium difficile* infections, urinary tract infections, sexually transmitted infections, foreign body infections, osteomyelitis, lyme disease, topical infections, opthalmological infections, tuberculosis and tropical diseases (e.g. malaria), and notably for the prevention or treatment (especially for the treatment) of a bacterial infection selected from the group consisting of respiratory tract infections, otitis media, meningitis, skin and soft tissue infections (whether complicated or uncomplicated), pneumonia (including hospital acquired pneumonia) and bacteremia.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I.

Any reference to a compound of formula I is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment (and notably for the treatment) of a bacterial infection in a patient comprising the administration to said patient of a pharmaceutically active amount of a compound of formula I or a pharmaceutically acceptable salt thereof.

Besides, any preferences and (sub-)embodiments indicated for the compounds of formula I (whether for the compounds themselves, salts thereof, compositions containing the compounds or salts thereof, uses of the compounds or salts thereof, etc.) apply *mutatis mutandis* to the compounds of formula $I_P$, the compounds of formula $I_{CE}$ and the compounds of formula $I_{CEP}$.

Moreover, the compounds of formula I may also be used for cleaning purposes, e.g. to remove pathogenic microbes and bacteria from surgical instruments or to make a room or an area aseptic. For such purposes, the compounds of formula I could be contained in a solution or in a spray formulation.

The compounds of formula I can be manufactured in accordance with the present invention using the procedures described hereafter.

Preparation of Compounds of Formula I

Abbreviations:

The following abbreviations are used throughout the specification and the examples:

Ac acetyl
AcOH acetic acid
AD-mix α 1,4-bis(dihydroquinine)phthalazine, $K_3Fe(CN)_6$, $K_2CO_3$ and $K_2OsO_4.2H_2O$
AD-mix β 1,4-bis(dihydroquinidine)phthalazine, $K_3Fe(CN)_6$, $K_2CO_3$ and $K_2OsO_4.2H_2O$
Alloc allyloxycarbonyl
aq. aqueous
Boc tert-butoxycarbonyl
Cbz benzyloxycarbonyl
CC column chromatography over silica gel
CDI 1,1'-carbonyldiimidazole
DBU 1,8-diazabicyclo(5.4.0)undec-7-ene
DCC N,N'-dicyclohexylcarbodiimide
DCE 1,2-dichloroethane
DCM dichloromethane
DEAD diethyl azodicarboxylate
DIAD diisopropyl azodicarboxylate
DIBAH diisobutylaluminium hydride
DIPEA N,N-diisopropylethylamine
DMAP 4-dimethylaminopyridine
DMF N,N-dimethylformamide
DMSO dimethylsulfoxide
DPPA diphenyl phosphoryl azide
EA ethyl acetate
EDC 1-(3-dimethylaminopropyl)-3-ethylcarbodiimide hydrochloride
ESI Electron Spray Ionisation
eq. equivalent
ether diethyl ether
Et ethyl
EtOH ethanol
Fmoc 9-fluorenylmethoxycarbonyl
HATU O-(7-azabenzotriazol-1-yl)-N,N,N',N'-tetramethyluronium hexafluorophosphate
Hex hexane
Hept heptane
HOBT 1-hydroxybenzotriazole hydrate
HV high vacuum conditions
KHMDS potassium hexamethyldisilazide
LAH lithium aluminium hydride
LC liquid chromatography
LiHMDS lithium hexamethyldisilazide
MCPBA meta-chloroperbenzoic acid
Me methyl
MeCN acetonitrile
MeOH methanol
MS Mass Spectroscopy
Ms methanesulfonyl (mesyl)
n-BuLi n-butyl lithium
NMO N-methyl-morpholine N-oxide
NMP N-methylpyrrolidin-2-one
org. organic
Pd/C palladium on carbon
$Pd(OH)_2$/C palladium dihydroxide on carbon
Ph phenyl
Pht phthaloyl
Pyr pyridine
rac racemic
rt room temperature
sat. saturated
T3P® n-propanephosphonic acid anhydride
TBAF tetrabutylammonium fluoride
TBDMS tert-butyldimethylsilyl
TBDPS tert-butyldiphenylsilyl
tBu tert-butyl
TEA triethylamine
TEMPO 2,2,6,6-tetramethyl-1-piperidinyloxy
Tf trifluoromethanesulfonyl (triflyl)

TFA trifluoroacetic acid
THF tetrahydrofuran
TLC thin layer chromatography
Ts para-toluenesulfonyl
General Reaction Techniques:
General Reaction Technique 1 (Amino Deprotection):

The benzyl carbamates are deprotected by hydrogenolysis over a noble metal catalyst (e.g. Pd/C or Pd(OH)$_2$/C). The Boc group is removed under acidic conditions such as HCl in an organic solvent such as MeOH or dioxane, or TFA neat or diluted in a solvent such DCM. The Alloc group is removed in presence of tetrakis (triphenylphosphine)palladium(0) in presence of an allyl cation scavenger such as morpholine, dimedone or tributyltin hydride between 0° C. and 50° C. in a solvent such as THF.

The N-benzyl protected amines are deprotected by hydrogenolysis over a noble catalyst (e.g. Pd(OH)$_2$/C).

The N-acetyl protecting group is removed under basic conditions such as Na$_2$CO$_3$, LiOH or NaOH in aq. MeOH or THF, or under acidic conditions such as aq. HCl in THF.

The Fmoc group is removed by treatment with an organic base such as piperidine or morpholine in a solvent such as DMF or THF.

Further general methods to remove amine protecting groups have been described in *Protecting Groups in Organic Synthesis*, 3$^{rd}$ Ed (1999), 494-653; T. W. Greene, P. G. M. Wuts; (Publisher: John Wiley and Sons, Inc., New York, N.Y.).

General Reaction Technique 2 (Activation of an Alcohol and Substitution with an Amine or an Azide):

The alcohol is reacted with MSCl, TfCl or TsCl in presence of a base such as TEA in a dry aprotic solvent such as Pyr, THF or DCM between –30° C. and 50° C. In the case of the triflate or mesylate, Tf$_2$O or Ms$_2$O can also be used. These sulfonates can be reacted with sodium iodide in a ketone such as acetone or 2-butanone, in MeCN or in DMF between 40° C. and 120° C. delivering the corresponding iodide derivatives. Once activated (either as a sulphonate or a iodide derivative), the alcohol can be reacted with an amine or sodium azide in presence of an organic base such as DIPEA or TEA or an inorganic base such as sodium carbonate in a solvent such as DMSO or DMF between 20° C. and 100° C. Alternatively, the azide can also be obtained by activation of the alcohol under Mitsunobu conditions in presence of PPh$_3$ and DEAD or DIAD in a solvent such as THF, DMF, DCM or DME between –20° C. and 60° C. as reviewed by O. Mitsunobu, in *Synthesis* (1981), 1 and reaction with DPPA.

General Reaction Technique 3 (Reductive Amination):

The reaction between the amine and the aldehyde or ketone is performed in a solvent system allowing the removal of the formed water through physical or chemical means (e.g. distillation of the solvent-water azeotrope or presence of drying agents such as molecular sieves, MgSO$_4$ or Na$_2$SO$_4$). Such a solvent system consists typically in toluene, Hex, THF, DCM or DCE or in a mixture of solvents such as MeOH-DCE. The reaction can be catalyzed by traces of acid (usually AcOH). The intermediate imine is reduced with a suitable reducing agent (e.g. NaBH$_4$, NaBH$_3$CN, or NaBH(OAc)$_3$) or through hydrogenation over a noble catalyst such as Pd/C. The reaction is carried out between –10° C. and 110° C., preferably between 0° C. and 60° C. The reaction can also be carried out in one pot. It can also be performed in protic solvents such as MeOH or water in presence of a picoline-borane complex (*Tetrahedron* (2004), 60, 7899-7906).

General Reaction Technique 4 (Alkylation of an Amine):

The amine derivative is reacted with an alkyl or alkenyl halide such as allyl iodide in presence of an inorganic base such as K$_2$CO$_3$ or an organic base such as TEA in a solvent such as THF between 0° C. and 80° C. In the particular case of a carbamate, the reaction is performed in presence of NaH between 0° C. and rt. Further details can be found in *Comprehensive Organic Transformations. A guide to Functional Group Preparations*; 2$^{nd}$ Edition, R. C. Larock, Wiley-VC; New York, Chichester, Weinheim, Brisbane, Singapore, Toronto, 1999. Section Amines p. 779.

General Reaction Technique 5 (Cis Dihydroxylation):

The diol is obtained by dihydroxylation of the corresponding alkenyl derivative using a catalytic amount of osmium tetroxide in the presence a co-oxidant such as NMO in aq. solvent such as an acetone-water or DCM-water mixture (see Cha, J. K. Chem. Rev. (1995), 95, 1761-1795). The chiral cis-diols are obtained by using AD-mix α or AD-mix β in presence of methanesulfonamide in a water/2-methyl-2-propanol mixture as described in *Chem. Rev.* (1994), 94, 2483. The sense of induction relies on the chiral ligand contained in the AD mixture, either a dihydroquinine-based ligand in AD-mix α or a dihydroquinidine-based ligand in AD-mix β.

General Reaction Technique 6 (Oxazolidinone Formation):

The 1,2-aminoalcohol derivative is reacted with phosgene, diphosgene or triphosgene. This reaction is preferably carried out in a dry aprotic solvent such as DCM or THF in presence of an organic base such as TEA or Pyr and at a temperature between –30° and +40° C.

Alternatively, the 1,2-aminoalcohol derivative is reacted with CDI or N,N'-disuccinimidyl carbonate in a dry aprotic solvent such as DCM or THF in presence of an organic base such as TEA or Pyr and at a temperature between –30° and +80° C.

General Reaction Technique 7 (Amine Protection):

Amines are usually protected as carbamates such as Alloc, Cbz, Boc or Fmoc. They are obtained by reacting the amine with allyl or benzyl chloroformate, di-tert-butyl dicarbonate or Fmoc chloride in presence of a base such as NaOH, TEA, DMAP or imidazole. They can also be protected as N-benzyl derivatives by reaction with benzyl bromide or chloride in presence of a base such as Na$_2$CO$_3$ or TEA. Alternatively, N-benzyl derivatives can be obtained through reductive amination in presence of benzaldehyde (see general reaction technique 3).

Further strategies to introduce other amine protecting groups have been described in *Protecting Groups in Organic Synthesis*, 3rd Ed (1999), 494-653; T. W. Greene, P. G. M. Wuts; (Publisher: John Wiley and Sons, Inc., New York, N.Y.).

General Reaction Technique 8 (Reduction of Carboxylates into Alcohols):

The ester is reduced with a boron or aluminium hydride reducing agent such as LiBH$_4$ or LiAlH$_4$ in a solvent such as THF between –20° C. and 40° C. Alternatively, the ester function is hydrolyzed into its corresponding acid using an alkali hydroxide such as NaOH, KOH or LiOH in water or in a mixture of water with polar protic or aprotic organic solvent such as THF or MeOH between –10° C. and 50° C. The resulting carboxylic acid is further reduced into the corresponding alcohol using a borane derivative such as a BH$_3$.THF complex in a solvent such as THF between –10° C. and 40° C.

General Reaction Technique 9 (Formation of Aldehydes):

The primary alcohols can be transformed into their corresponding aldehydes through oxidation under Swern (see D. Swern et al., *J. Org. Chem.* (1978), 43, 2480-2482) or Dess Martin (see D. B. Dess and J. C. Martin, *J. Org. Chem.* (1983), 48, 4155) conditions, respectively Alternatively, the esters can be transformed into their corresponding aldehydes by controlled reduction with a bulky hydride reagent such as DIBAH.

General Reaction Technique 10 (Ring Closure):

The alcohol derivative is dissolved in THF or DMF and treated with tBuOK and the solution is heated between 60° C. to 100° C. for one hour. The reaction mixture is quenched with a sat. $NH_4Cl$ solution.

General Reaction Technique 10a (Ring Closure):

The amine derivative is dissolved in NMP or DMF and treated with DIPEA or $K_2CO_3$ and the solution is heated between 60° C. to 100° C. for one hour. The reaction mixture is quenched with a sat. $NH_4Cl$ solution.

General Reaction Technique 11 (Hydroxy Deprotection):

The silyl ether groups are removed either using fluoride anion sources such as TBAF in THF between 0° C. and 40° C. or HF in MeCN between 0° C. and 40° C. or using acidic conditions such as AcOH in THF/MeOH or HCl in MeOH. Further methods to remove the TBDMS and TBDPS groups are given in *Protecting Groups in Organic Synthesis*, $3^{rd}$ Ed (1999), 133-139 and 142-143 respectively; T. W. Greene, P. G. M. Wuts; (Publisher: John Wiley and Sons, Inc., New York, N.Y.). Further general methods to remove alcohol protecting groups are described in *Protecting Groups in Organic Synthesis*, $3^{rd}$ Ed (1999), 23-147; T. W. Greene, P. G. M. Wuts; (Publisher: John Wiley and Sons, Inc., New York, N.Y.).

General Reaction Technique 12 (Oxazolidine Ring Formation Using Glycidyl Esters):

The aniline carbamate is reacted in a dry solvent such as THF with a strong organic base such as n-BuLi between −100° C. and −30° C. or with tBuOLi, tBuOK or KEIMDS between −100° C. and −30° C. The anion is reacted at these temperatures with the required glycidyl esters and allowed to reach rt.

General Reaction Technique 13 (Reduction of Azides into Amines):

The azides are hydrogenated over a noble metal catalyst such as Pd/C in solvent such as MeOH or EA. In case the molecule is containing an unsaturated double or triple bond, the reduction can be performed using $PPh_3$ in presence of water as described in *J. Med. Chem.* (1993), 36, 2558-68.

General Reaction Technique 14 (Wittig):

The required phosphonium salt is treated in a solvent such as water with an inorganic base such as NaOH. The corresponding phosphorane is collected by filtration and dried in vacuo. It is reacted with the required aldehyde in an aprotic solvent such as THF, DCM or toluene between 0° C. and 90° C. Alternatively the Wittig-Horner variant of the reaction can be used wherein the phosphono ester (generated from the corresponding bromide and triethylphosphite) is reacted with the adehyde in presence of a base such as NaH or NaOMe in a solvent such as ether or THF between 0° C. and 50° C.

General Reaction Technique 15 (Protection of Alcohols):

The alcohols are protected as silyl ether (usually TBDMS or TBDPS). The alcohol is reacted with the required silyl chloride reagent (TBDMSCl or TBDPSCl) in presence of a base such as imidazole or TEA in a solvent such as DCM, THF or DMF between 10° C. and 40° C.

Further strategies to introduce other alcohol protecting groups have been described in *Protecting Groups in Organic Synthesis* $3^{rd}$ Ed (1999), 23-147; T. W. Greene, P. G. M. Wuts; (Publisher: John Wiley and Sons, Inc., New York, N.Y.).

General Reaction Technique 16 (Intramolecular Ring Closure According to Buchwald):

In the case wherein an alcohol is ring closed, the aromatic halide (Cl, Br, I) is reacted in presence of a palladium catalyst such as palladium (II) acetate, in presence of a dialkylphophinobiaryl ligand such as [1,1']binaphthalenyl-2-yl-di-tert-butyl-phosphane and in presence of a base such as $K_2CO_3$ or $Cs_2CO_3$ between +20° C. and +100° C., as described in *J. Am. Chem. Soc.* (2001), 123, 12202-12206.

In the case wherein an amine is ring closed, the aromatic halide (Cl, Br, I) is reacted in presence of CuI, in presence of $Cs_2CO_3$ between +20° C. and +100° C., as described in *J. Am. Chem. Soc.* (2006), 128, 8742-8743.

General Reaction Technique 17 (Amide Coupling):

The carboxylic acid is reacted with the amine in presence of an activating agent such as DCC, EDC, n-propylphosphonic cyclic anhydride, HATU or di-(N-succinimidyl)-carbonate, in a dry aprotic solvent such as DCM, MeCN or DMF between −20° C. and +60° C. (see G. Benz in *Comprehensive Organic Synthesis*, B. M. Trost, I. Fleming, Eds; Pergamon Press: New York (1991), vol. 6, p. 381). Alternatively, the carboxylic acid can be activated by conversion into its corresponding acid chloride by reaction with oxalyl chloride or thionyl chloride neat or in a solvent like DCM between −20° and +60° C. Further activating agents can be found in *Comprehensive Organic Transformations. A guide to Functional Group Preparations;* $2^{nd}$ Edition, R. C. Larock, Wiley-VC; New York, Chichester, Weinheim, Brisbane, Singapore, Toronto, 1999. Section nitriles, carboxylic acids and derivatives, p. 1941-1949.

General Reaction Technique 18 (Oxidation of Alcohols into Acids):

Alcohols can be directly oxidized into their corresponding acids by a variety of methods as described in *Comprehensive Organic Transformations. A guide to Functional Group Preparations;* 2nd Edition, R. C. Larock, Wiley-VC; New York, Chichester, Weinheim, Brisbane, Singapore, Toronto, 1999. Section nitriles, carboxylic acids and derivatives, p. 1646-1648. Among them, [bis(acetoxy)iodo]benzene in presence of TEMPO, the Jones reagents ($CrO_3/H_2SO_4$), $NaO_4$ in presence of $RuCl_3$, $KMnO_4$ or pyridine $H_2Cr_2O_7$ are frequently used.

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

Sections a) to g) hereafter describe general methods for preparing compounds of formula I. In these sections, the symbols A, $R^1$, W, B, G, m, n, p and q have the same meanings as in formula I unless mentioned otherwise.

a) The compounds of formula I and B is $(CH_2)_q$ can be obtained by deprotecting the compounds of formula II

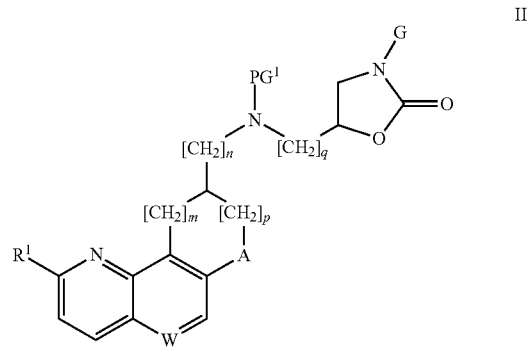

wherein A is O, NH or N—PG⁰ and PG⁰ and PG¹ each represent an amino protecting group such as Boc, Cbz, Fmoc or benzyl, following general reaction technique 1.

b) The compounds of formula I wherein B is (CH$_2$)$_q$ can be obtained by reacting the compounds of formula III

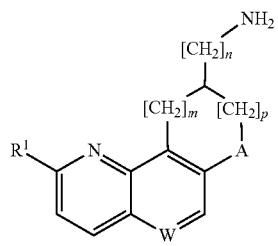

wherein A is O or NPG⁰, wherein PG⁰ is an amino protecting group such as Cbz, Boc, Fmoc or benzyl, with the compounds of formula IV

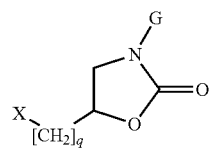

wherein X represents a halogen such as iodine or bromine, or a group of the formula OSO$_2$R$^a$ wherein R$^a$ represents methyl, trifluoromethyl or tolyl, following general reaction technique 2. In the cases wherein A is N—PG⁰, the protecting group can be removed following general reaction technique 1.

c) The compounds of formula I wherein B is (CH$_2$)$_q$ can also be obtained by reacting the compounds of formula V

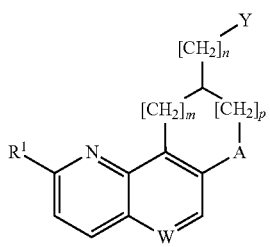

wherein A is O or N—PG⁰, PG⁰ is an amino protecting group such as Boc, Cbz, Fmoc or benzyl and Y represents a halogen such as iodine or bromine, or a group of the formula OSO$_2$R$^a$ wherein R$^a$ represents methyl, trifluoromethyl or tolyl, following general reaction technique 2, with the compounds of formula VI

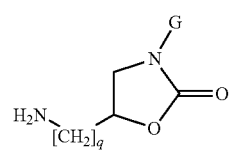

In the cases wherein A is N—PG⁰, the protecting group can be removed following general reaction technique 1.

d) The compounds of formula I wherein B is (CH$_2$)$_q$ can furthermore be obtained by reacting the compounds of formula VII

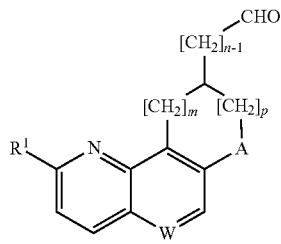

wherein A is O or N—PG⁰, PG⁰ being an amino protecting group such as Boc, Cbz, Fmoc or benzyl, with the previously mentioned compounds of formula VI following general reaction technique 3.

e) The compounds of formula I wherein A is O and p is 1 can be obtained by cyclising the compounds of formula VIII

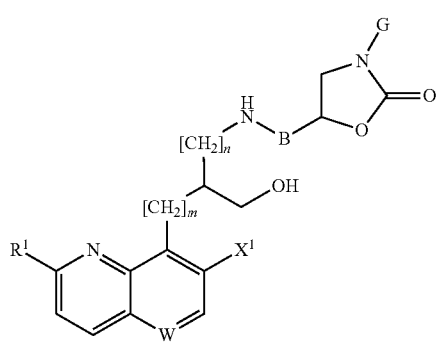

wherein X¹ represents halogen such as fluorine or bromine according to general reaction technique 10. Alternatively, the compounds of formula VIII can be N-protected according to general reaction technique 7, ring closed under Buchwald conditions according to general reaction technique 16 and finally N-deprotected according to general reaction technique 1.

f) The compounds of formula I wherein A is NH, p is 1 and B is (CH$_2$)$_q$ can be obtained by cyclising the compounds of formula IX

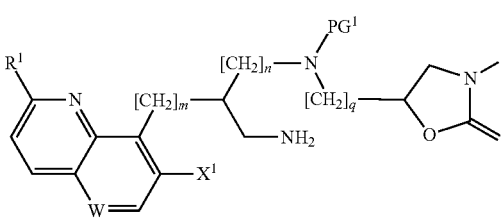

wherein X¹ represents halogen such as fluorine or bromine and PG¹ is an amino protecting group such as Boc, Cbz, Fmoc or benzyl according to general reaction technique 10 followed by removal of the amino protecting group according to general reaction technique 1.

g) The compounds of formula I wherein B is CO can be obtained by reacting the derivatives of formula III described previously with the derivatives of formula X

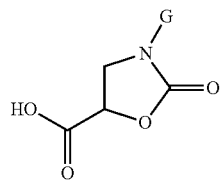

X according to general reaction technique 17. In the cases wherein A is N-PG⁰, the protecting group can be removed following general reaction technique 1.

The compounds of formula I thus obtained may, if desired, be converted into their salts, and notably into their pharmaceutically acceptable salts.

Besides, whenever the compounds of formula I are obtained in the form of mixtures of enantiomers, the enantiomers can be separated using methods known to one skilled in the art, e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min. Whenever the compounds of formula I are obtained in the form of mixtures of diasteromers they may be separated by an appropriate combination of silica gel chromatography, HPLC and crystallization techniques.

Preparation of the Compounds of Formulae II to X:

The compounds of formula II can be prepared as described in Scheme 1 hereafter.

Scheme 1

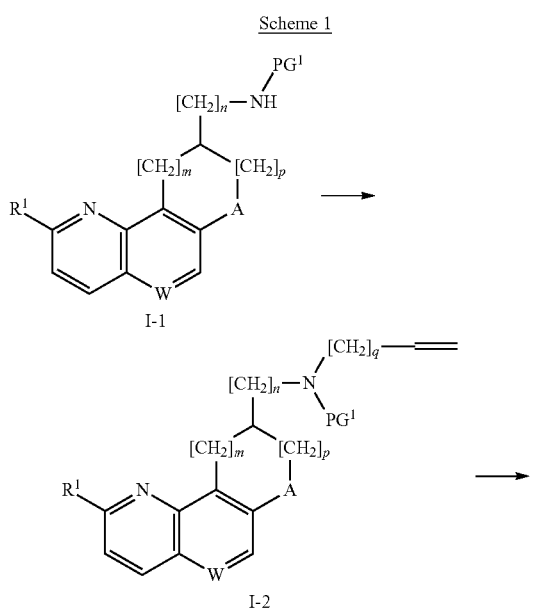

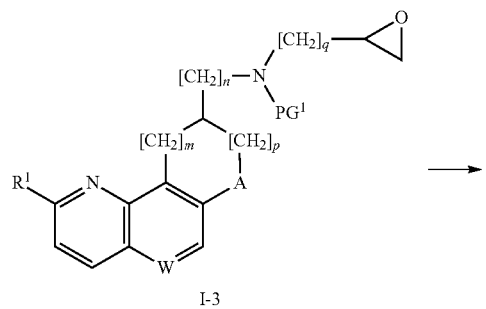

I-3

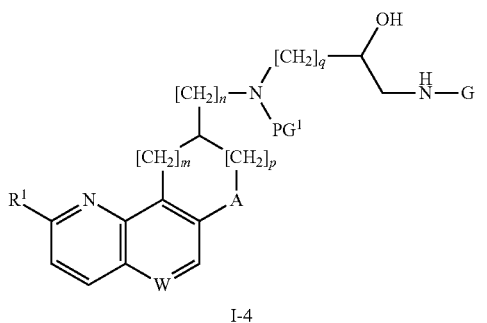

I-4

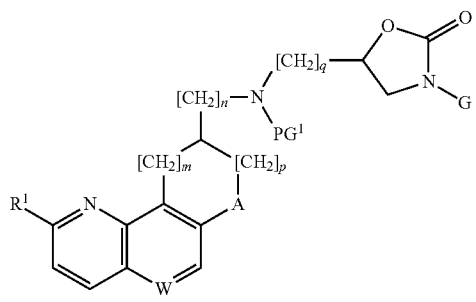

II

In Scheme 1, A represents O, NH or NPG⁰ and PG⁰ and PG¹ represent independently from each other an amino protecting group such as Boc, Fmoc, Cbz or benzyl.

The compounds of formula I-1 wherein A is O or N—PG⁰ can be transformed into the compounds of formula I-3 by reaction with allyl bromide or 4-bromo-1-butene according to general reaction technique 4, followed by cis-dihydroxylation according to general reaction technique 5, followed by activation of the primary alcohol function as a mesylate according to general reaction technique 2 and ring closure into the epoxide in presence of a base such as $Na_2CO_3$ or TEA. Alternatively the compounds of formula I-3 wherein q is 1 might be obtained by reacting intermediates of formula I-1 with epichlorhydrin. The epoxides of formula I-3 can be further reacted with an aniline of formula G-NH₂ and the resulting amino alcohols of formula I-4 can be transformed into the compounds of formula II wherein A is O or N—PG⁰ according to general reaction technique 6. If A is N—PG⁰, the amino protecting group can be removed according to general reaction technique 1.

The compounds of formula III and I-1 wherein m is 1, n is 1 and p is 1 can be prepared as described in Scheme 2 hereafter.

Scheme 2

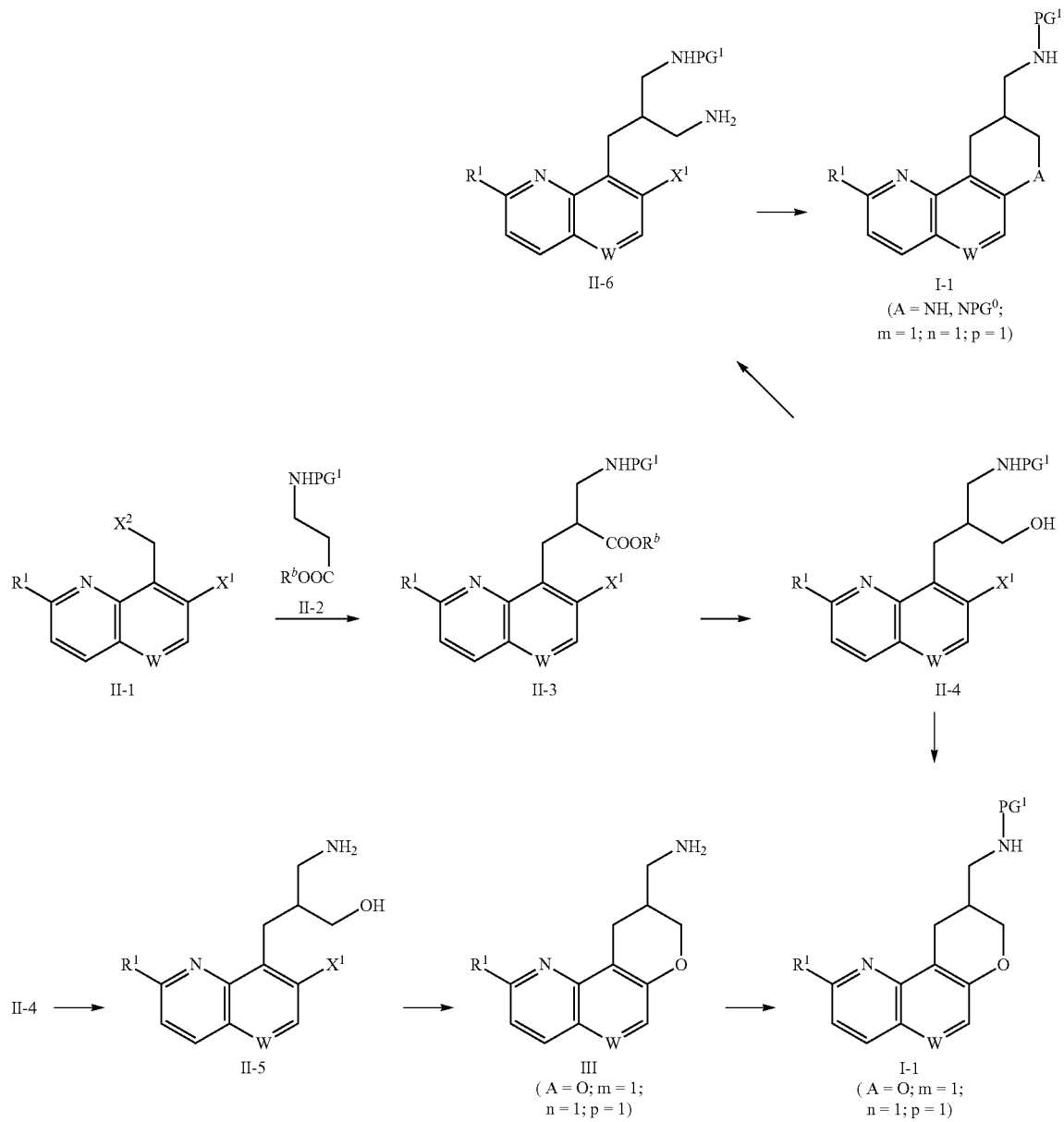

In Scheme 2, $X^1$ and $X^2$ represent independently from each other halogen such as fluorine (e.g. for $X^1$) or bromine (e.g. for $X^2$), $R^b$ represents alkyl or benzyl and $PG^1$ represents an amino protecting group such as Cbz, Boc, Fmoc or benzyl.

The intermediates of formula II-1 can be reacted with the β-alanine derivatives of formula II-2 (e.g. N-(tert-butoxycarbonyl)-β-alanine methyl ester; commercial) in the presence of a strong base such as LiHDMS below −50° C. in a dry solvent such as THF. The resulting amino ester derivatives of formula II-3 can be reduced into the corresponding alcohol derivatives of formula II-4 according to general reaction technique 8. The amino protecting group can be removed according to general reaction technique 1 and the resulting amino alcohols of formula II-5 can then be cyclised according to general reaction techniques 10a or 16. The compounds of formula I-1 can be obtained by protection of the compounds of formula III according to general reaction technique 7. Alternatively they can be obtained by cyclising the intermediates of formula II-4 in presence of a base such as $K_2CO_3$ or NaH. The compounds of formula I-1 wherein A is NH or $NPG^0$ can be obtained by transforming the compounds of formula II-4 into their corresponding mesylates and amines of formula II-6 according to general reaction techniques 2 and 13. These latter intermediates can be cyclised according to general reaction technique 10 or 10a, affording the compounds of formula I-1 wherein A is NH. The compounds of formula I-1 wherein A is $NPG^0$ can be obtained by subsequent protection according to general reaction technique 7.

The compounds of formula III wherein m is 0, p is 1 and n is 2 can be prepared as described in Scheme 3 hereafter.

Scheme 3

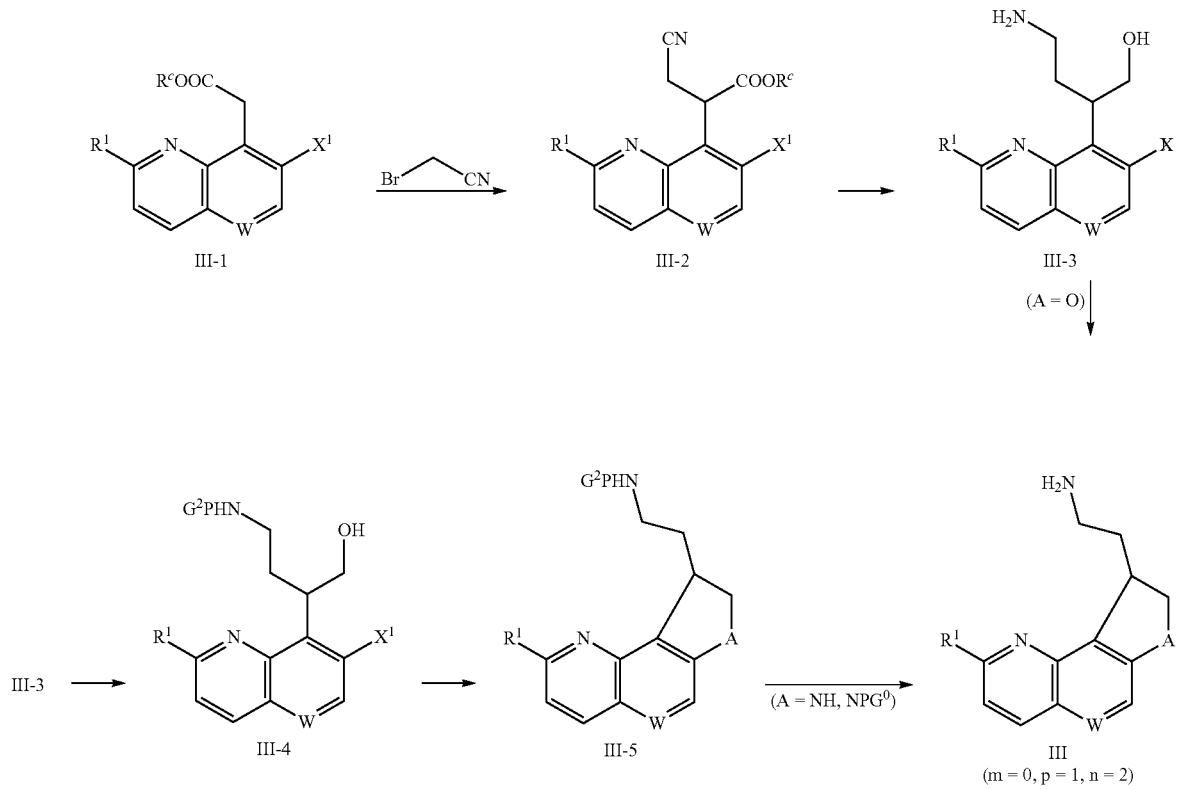

In Scheme 3, $R^c$ represents alkyl, $X^1$ represents halogen such as fluorine, chlorine or bromine and $PG^0$ and $PG^2$ each represent an amino protecting group such as Cbz, Boc, Fmoc or benzyl.

The esters of formula III-1 can be reacted with bromoacetonitrile in presence of a strong base such as LiHDMS below −50° C. in a dry solvent such as THF. The resulting nitrile derivatives of formula III-2 can be reduced with LAH in presence of $AlCl_3$ affording the amino alcohols of formula III-3 which can then be cyclised into the derivatives of formula III according to general reaction technique 10. The amine function of the compounds of formula III-3 can be protected according to general reaction technique 7 and the alcohol function can be transformed into the corresponding amine according to general reaction techniques 2 and 13 and further be cyclised according to general reaction techniques 10a or 16. The resulting derivatives of formula III-5 wherein A is NH can optionally be protected according to general reaction technique 7 and finally the protecting group on the primary amine is removed according to general reaction technique 1.

The compounds of formula III wherein m is 0 and n and p are each 1 can be prepared as described in Scheme 4 hereafter.

Scheme 4

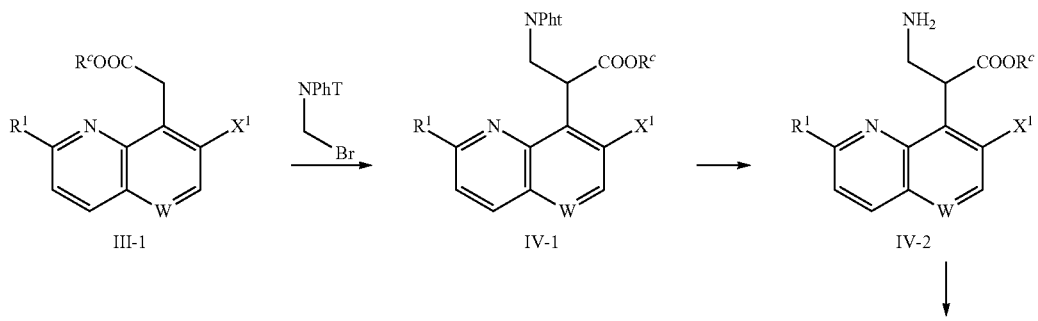

-continued

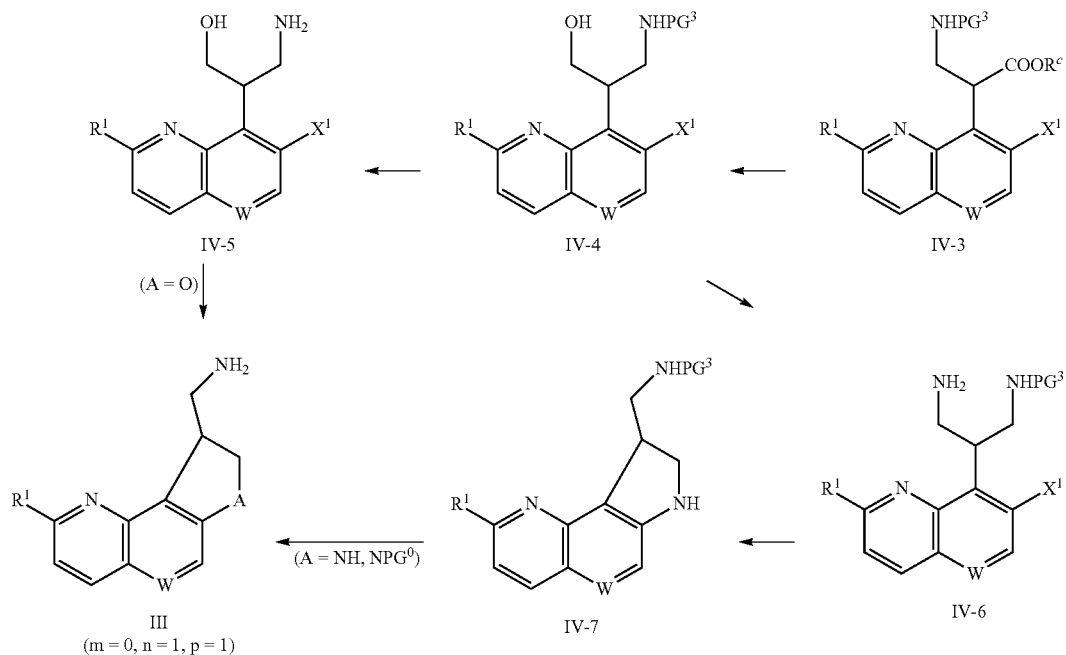

In Scheme 4, $R^c$ represents alkyl, $X^1$ represents halogen such as fluorine, bromine or chlorine and $PG^3$ represents an amino protecting group such as Cbz, Boc, Fmoc or benzyl.

The intermediates of formula III-1 can be reacted with N-(bromomethyl)phthalimide (commercial) in presence of a strong base such as LiHDMS below −50° C. in a dry solvent such as THF. The resulting phthalimido derivatives of formula IV-1 can be reacted with a hydrazine derivative such as hydrazine hydrate or N-methyl hydrazine in a solvent such as ethanol or DCE between 40° C. and 80° C. affording the corresponding amino derivatives of formula IV-2, which can be protected following general reaction technique 7. The intermediates of formula IV-3 can be reduced following general reaction technique 8, the protecting group can be removed following general reaction technique 1, and the compounds can then be ring closed using general reaction technique 10 to yield the desired compounds of formula III wherein A is O. The compounds of formula III wherein A is NH or NPG⁰ can be obtained by transforming the alcohol derivatives of formula IV-4 into the corresponding amino derivatives of formula IV-6 according to general reaction techniques 2 and 13 followed by cyclisation according general reaction technique 10. The resulting derivatives of formula IV-7 wherein A is NH can optionally be protected according to general reaction technique 2 and finally the protecting group on the primary amine can be removed according to general reaction technique 1.

The compounds of formula III wherein p is 0, m is 1 and n is 1 or 2 can be prepared as described in Scheme 4a hereafter.

Scheme 4a

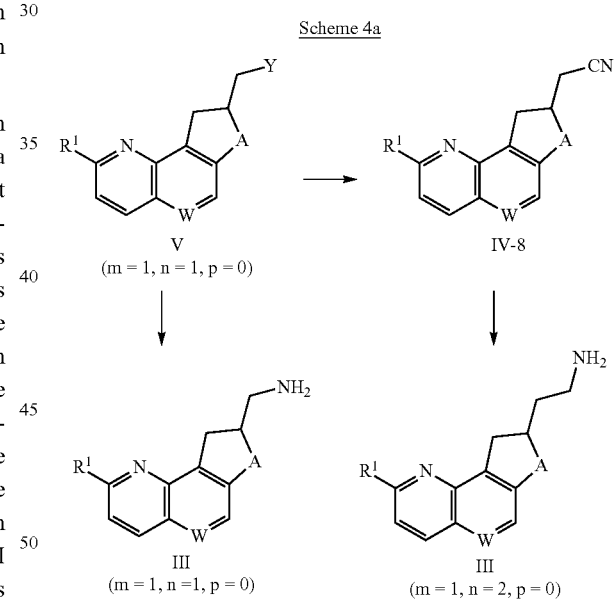

The compounds of formula V wherein m is 1, n is 1, p is 0, Y is $OSO_2R^a$ wherein $R^a$ represents methyl, trifluoromethyl or tolyl, A is O or NPG⁰ wherein PG⁰ is an amino protecting group such as Cbz, Boc, Fmoc or benzyl can be reacted with an alkali metal cyanide, affording the corresponding nitrile derivatives of formula IV-8 which can further be transformed into the corresponding amine derivatives of formula III wherein m is 1, n is 2 and p is 0 by reaction with an hydride reagent such as LAH. The compounds of formula V can also be transformed into the corresponding amine derivatives of formula III wherein m and n are each 1 and p is 0 according to general reaction techniques 2 and 13.

The compounds of formulae V and VII wherein n is 1 and p is 1 can be prepared as described in Scheme 5 hereafter.

Scheme 5

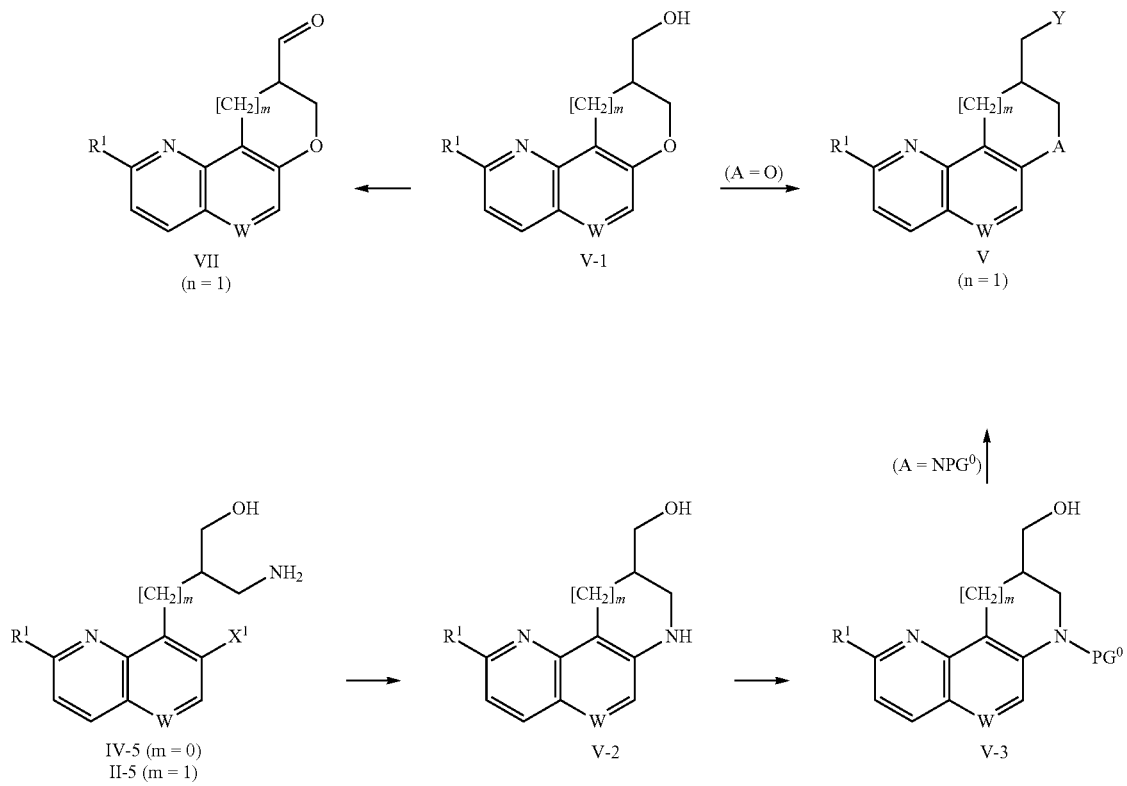

In Scheme 5, $PG^0$ represents an amino protecting group such as Boc, Fmoc, Cbz or benzyl and $X^1$ represents halogen such as fluorine or bromine.

The compounds of formula V wherein A is O, m is 0 or 1 and n is 1 and the compounds of formula VII wherein m is 0 or 1 and n is 1 can be obtained from the corresponding alcohol derivatives of formula V-1 by either activation of the alcohol function or oxidation into the corresponding aldehydes, following general reaction techniques 2 and 9 respectively.

The compounds of formula V wherein A is $N-PG^0$, m is 0 or 1 and n is 1 can be obtained by activation of the alcohol function of the derivatives of formula V-3 following general reaction technique 2. The starting alcohols of formula V-3 can be obtained from the precursors of formula V-2 according to the general reaction technique 7. The compounds of formula V-2 can be obtained from compounds of formula II-5 or IV-5 by cyclisation using general reaction technique 10a or 16. The compounds of formula V-2 can also be obtained from the corresponding protected alcohols, obtained from the compounds of formula II-5 or IV-6 following general reaction technique 15, by intramolecular cyclisation according to the general reaction technique 16, followed by removal of the alcohol protection following general reaction technique 11.

Besides, the compounds of formula V wherein n is 2 and p is 1 can be prepared as described in Scheme 5a hereafter.

Scheme 5a

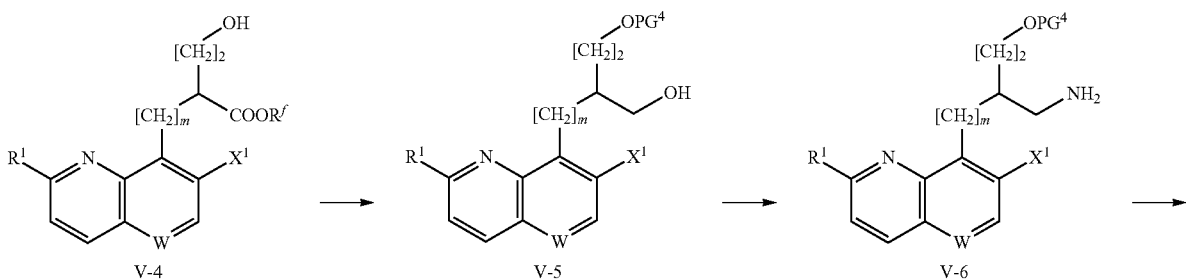

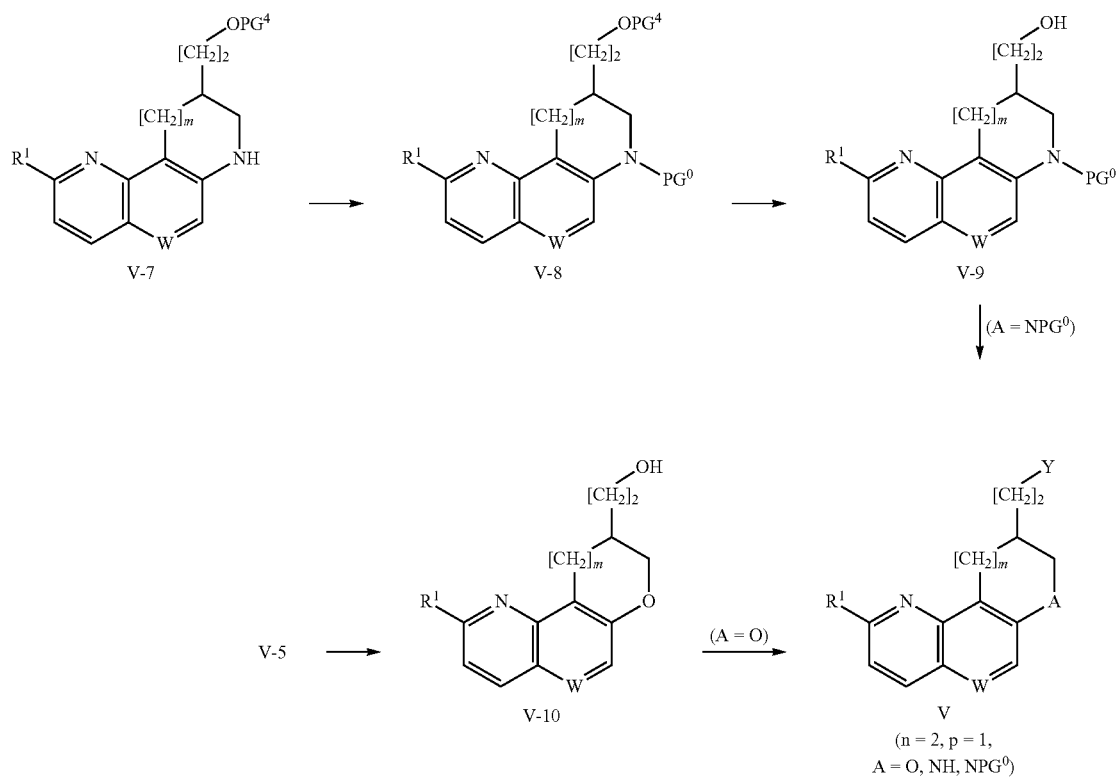

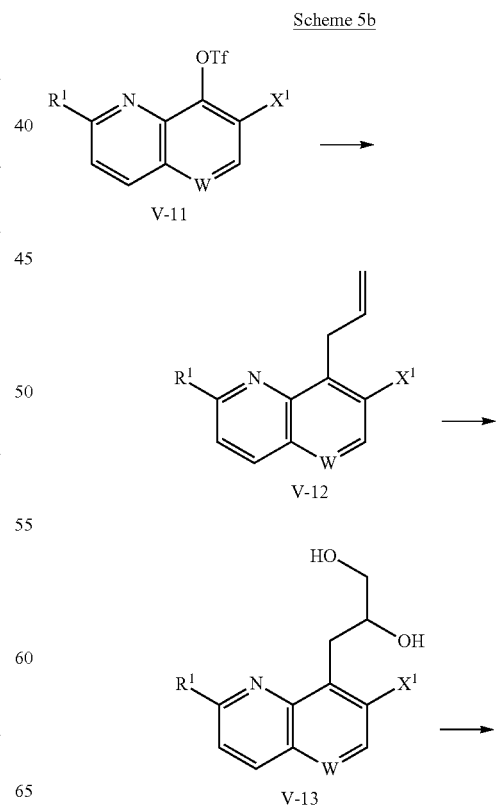

Scheme 5b

In Scheme 5a, PG⁰ represents an amino protecting group such as Boc, Fmoc, Cbz or benzyl, PG⁴ represents a hydroxy protecting group such as TBDMS or OCORg wherein $R^g$ is alkyl, $R^f$ represents alkyl or benzyl and $X^1$ represents halogen such as fluorine.

The compounds of formula V wherein A is N—PG⁰ can be obtained from the alcohol derivatives of formula V-4 after sequential protection of the alcohol function following general reaction technique 15 and reduction of the ester function following general reaction technique 8. The resulting alcohols derivatives of formula V-5 can be transformed into the corresponding amine derivatives of formula V-6 following general reaction techniques 2 and 13. The amine derivatives of formula V-6 can be cyclised into the derivatives of formula V-7 by treatment with a base such as DIPEA or $K_2CO_3$ (if W is N), or following general reaction technique 16 (if W is CH). The tricyclic derivatives of formula V-7 can be transformed into the compounds of formula V-8 following general reaction technique 7 and the alcohol protecting group can be removed following general reaction technique 11. The resulting alcohol derivatives of formula V-9 can then be transformed into the desired derivatives of formula V wherein A is NPG⁰ following general reaction technique 2. The derivatives of formula V-5 can also be directly cyclised using general reaction technique 10a or 16, affording, after removal of the alcohol protecting group following general reaction technique 11, the intermediate derivatives of formula V-10 which can be further transformed into the derivatives of formula V wherein A is O using general reaction technique 2.

The compounds of formula V wherein m is 1, n is 1 or 2 and p is 0 can be prepared as described in Scheme 5b hereafter.

-continued

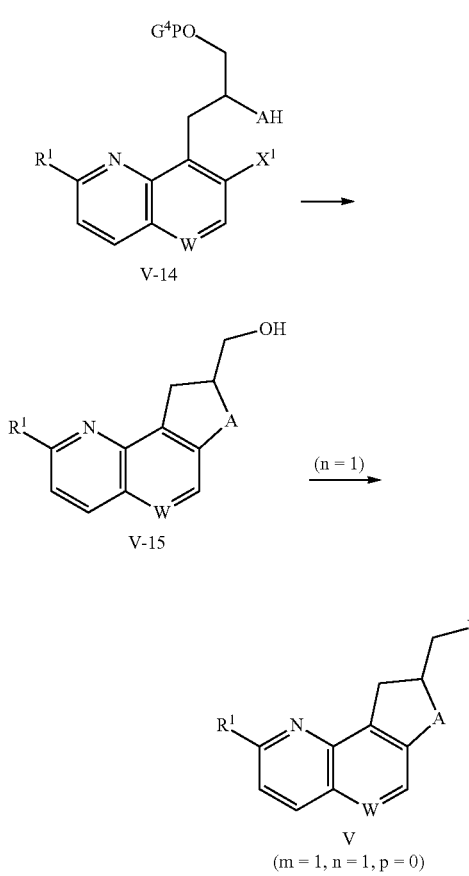

The triflate derivatives of formula V-11 (e.g. trifluoromethanesulfonic acid 3-chloro-6-methoxy-[1,5]naphthyridin-4-yl ester; prepared according to WO 2004/058144) can be transformed into the corresponding allyl derivatives of formula V-12 after reaction with allyltributyltin in presence of a cross coupling palladium catalyst such as $Pd(PPh_3)_4$. These intermediates can be transformed into the corresponding diols of formula V-13 using general reaction technique 5. The primary alcohol function of the latter can be protected using general reaction technique 15, affording the intermediates of formula V-14 wherein A is O. These derivatives can be transformed into the corresponding intermediates of formula V-14 wherein A is NH using general reaction techniques 2 and 13. The intermediates of formula V-14 can be cyclised into the derivatives of formula V-15 using general reaction technique 10 if A is O, or general reaction technique 10a or 16 if A is NH. In the case wherein A is NH, an amino protecting group ($PG^0$) should be introduced using general reaction technique 7. The alcohol function of the intermediates of formula V-15 can be activated using general reaction technique 2, affording the intermediates of formula V wherein n is 1. The intermediates of formula V wherein n is 2 can be obtained by reduction of the corresponding aldehydes of formula VII wherein n is 2 using general reaction technique 8 followed by activation of the alcohol using general reaction technique 2.

The compounds of formula VII can be obtained by oxidation of the corresponding alcohol derivatives of formulae V-1, V-3, V-9, V-10 and V-15 using general reaction technique 9 or, in the case of compounds of formula VII wherein m is 1, n is 2 and p is 0, by reduction of the nitrile derivatives of formula IV-8 with DIBAH.

The compounds of formula VIII wherein B is $(CH_2)_q$ can be prepared as described in Scheme 6 hereafter.

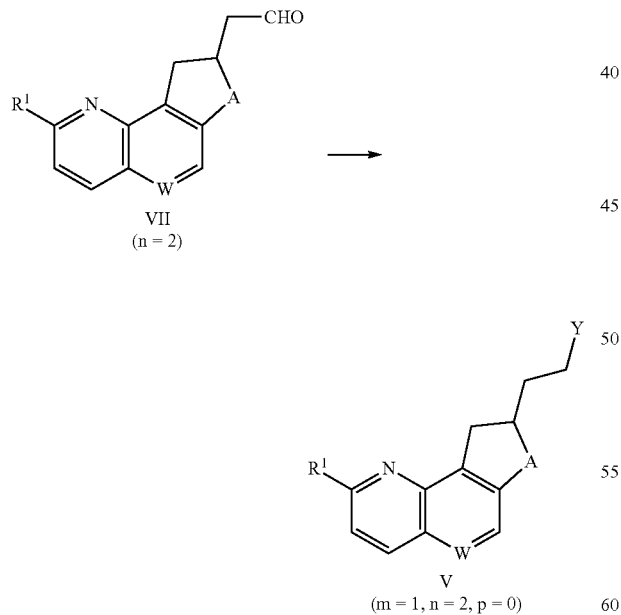

In Scheme 5b, A represents O, NH or N—$PG^0$ wherein $PG^0$ represents an amino protecting group such as Boc, Cbz, Fmoc or benzyl, $PG^4$ represents a hydroxy protecting group such as TBDMS or $OCOR^g$ wherein $R^g$ is alkyl and $X^1$ represents halogen such as chlorine.

Scheme 6

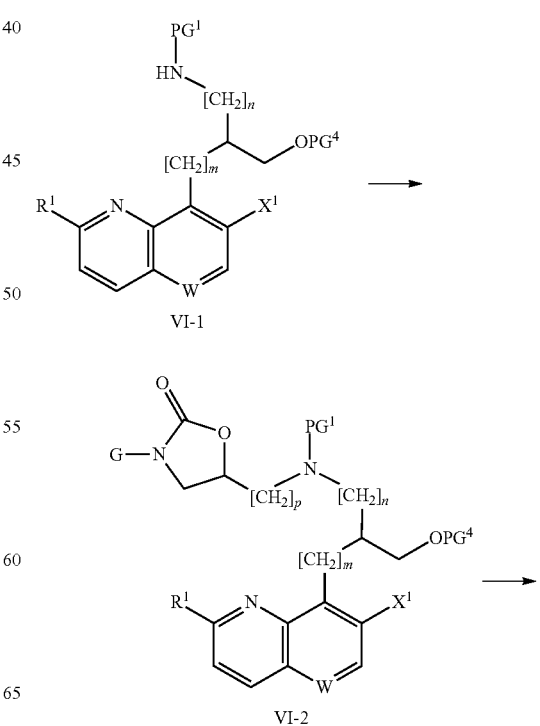

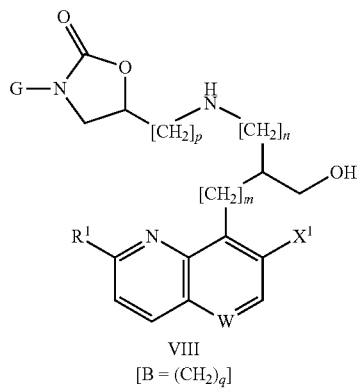

VIII
[B = (CH$_2$)$_q$]

In Scheme 6, $X^1$ is a halogen such as fluorine, chlorine or bromine, $PG^1$ is an amino protecting group such as Boc or Cbz and $PG^4$ is a hydroxy protecting group such as TBDMS.

The derivatives of formula VI-1 can be transformed into the corresponding derivatives of formula VI-2 following the same methods as described in Scheme 1 for the preparation of compounds of formula II. The compounds of formula VIII wherein B is (CH$_2$)$_q$ can then be obtained by deprotection of compounds of formula VI-2 using general reaction techniques 1 and 11.

The compounds of formula VIII wherein B is CO can be obtained by removing the amino protecting group from the abovementioned compounds of formula VI-1 using general reaction technique 1 followed by formation of the corresponding amide by reaction with the compounds of formula X according to general reaction technique 17. The compounds of formula VIII can then be obtained by deprotection of compounds of formula VI-2 using general reaction technique 11.

The compounds of formulae IV, VI and X can be prepared as described in Scheme 7 hereafter.

$OSO_2R^a$ wherein $R^a$ represents methyl, trifluoromethyl or tolyl.

The epoxides of formula VII-1 wherein $PG^5$ is $OCOR^g$ (e.g. glycidyl butyrate, commercial; or 3,4-epoxybutyl butyrate, prepared according to *J. Am. Chem. Soc.* (2005), 127(32), 11426-11435) can be reacted with the carbamates of formula GNHPG$^6$ (wherein PG$^6$ represents COOMe, Cbz or Boc) according to general reaction technique 12, affording the oxazolidinones of formula VII-4. Alternatively, the epoxides of formula VII-1 wherein $PG^5$ is a silyl protecting group (e.g. glycidyl tert-butyldimethylsilyl ether; commercial) can be reacted with the aniline derivatives of formula GNH$_2$ affording the amino alcohol derivatives of formula VII-2. These aminoalcohols can be transformed into the oxazolidinones of formula VII-3 according to general reaction technique 6 and the hydroxy protecting group can then be removed according to general reaction technique 11 to afford the compounds of formula VII-4. The alcohols can be sequentially transformed into the corresponding derivatives of formula IV wherein X is OMs, OTs, OTf or I and into the corresponding azide derivatives of formula VII-5 using general technique 2. The amine derivatives of formula VI can then be obtained after reduction of azide derivatives of formula VII-5 according to general reaction technique 13. Besides, the acids of formula X can be obtained by oxidation of the corresponding alcohols of formula VII-4 wherein q is 1 using general reaction technique 18.

The compounds of formula IX can be obtained by protecting the amine function of compounds of formula VIII wherein B is (CH$_2$)$_q$ according to general reaction technique 7, activation of the alcohol function and transformation into the corresponding azide according to general reaction technique 2 and transformation of the azide into the corresponding amine according to general reaction technique 13.

Preparation of the Starting Compounds:

The compounds of formula I-1 wherein A is O can be made from compounds of formula III by protection of the primary amine according to general reaction technique 7.

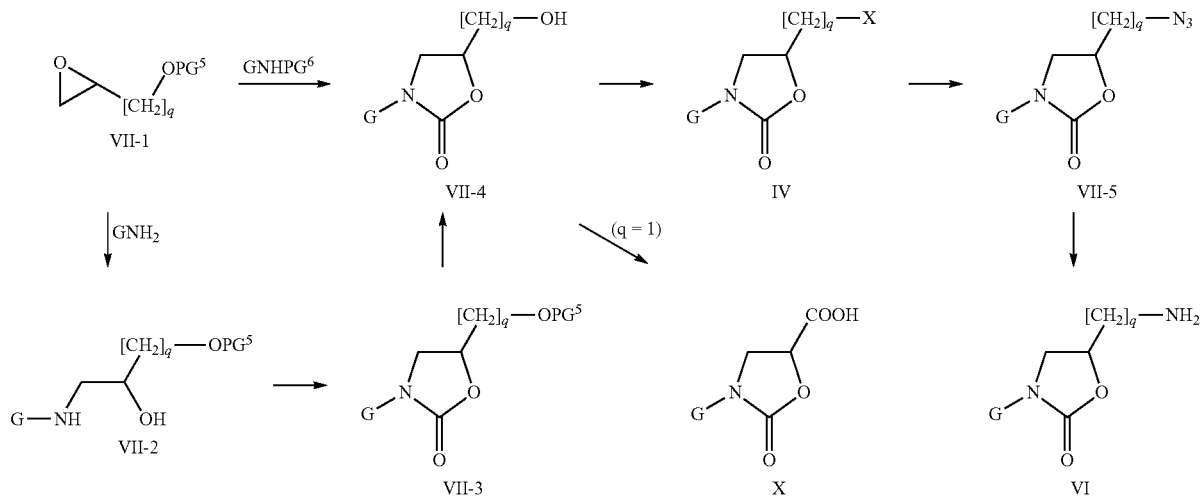

In Scheme 7, $PG^5$ represents a hydroxy protecting group such as TBDMS or $OCOR^g$ wherein $R^g$ is alkyl, $PG^6$ is $COOR^h$ wherein $R^h$ is alkyl or benzyl and X represents a halogen such as iodine or bromine, or a group of the formula The compounds of formula I-1 wherein A is N-PG$^0$, PG$^0$ being Boc, Cbz or Fmoc, can be made from the compounds of formula V following sequential formation of the corresponding azide (using general reaction technique 2) and the corresponding amine (using general reaction technique 13) followed by protection of the primary amine (using general reaction technique 7).

The compounds of formula II-1 wherein W is CH, $R^1$ is OMe and $X^1$ is F can be prepared according to WO 2008/003690. The compounds of formula II-1 wherein W is N, $R^1$ is OMe and $X^1$ is F can be prepared by reduction of the corresponding formyl derivatives (obtained according to WO 2006/032466) through reduction with $NaBH_4$ followed by reaction of the intermediate benzyl alcohols with $PBr_3$.

The compounds of formula III-1 wherein W is CH or N, $R^1$ is OMe and $X^1$ is F can be prepared according to WO 2007/081597 and WO 2007/122258.

The compounds of formulae V-4 and VI-1 can be obtained as described in Scheme 8 hereafter.

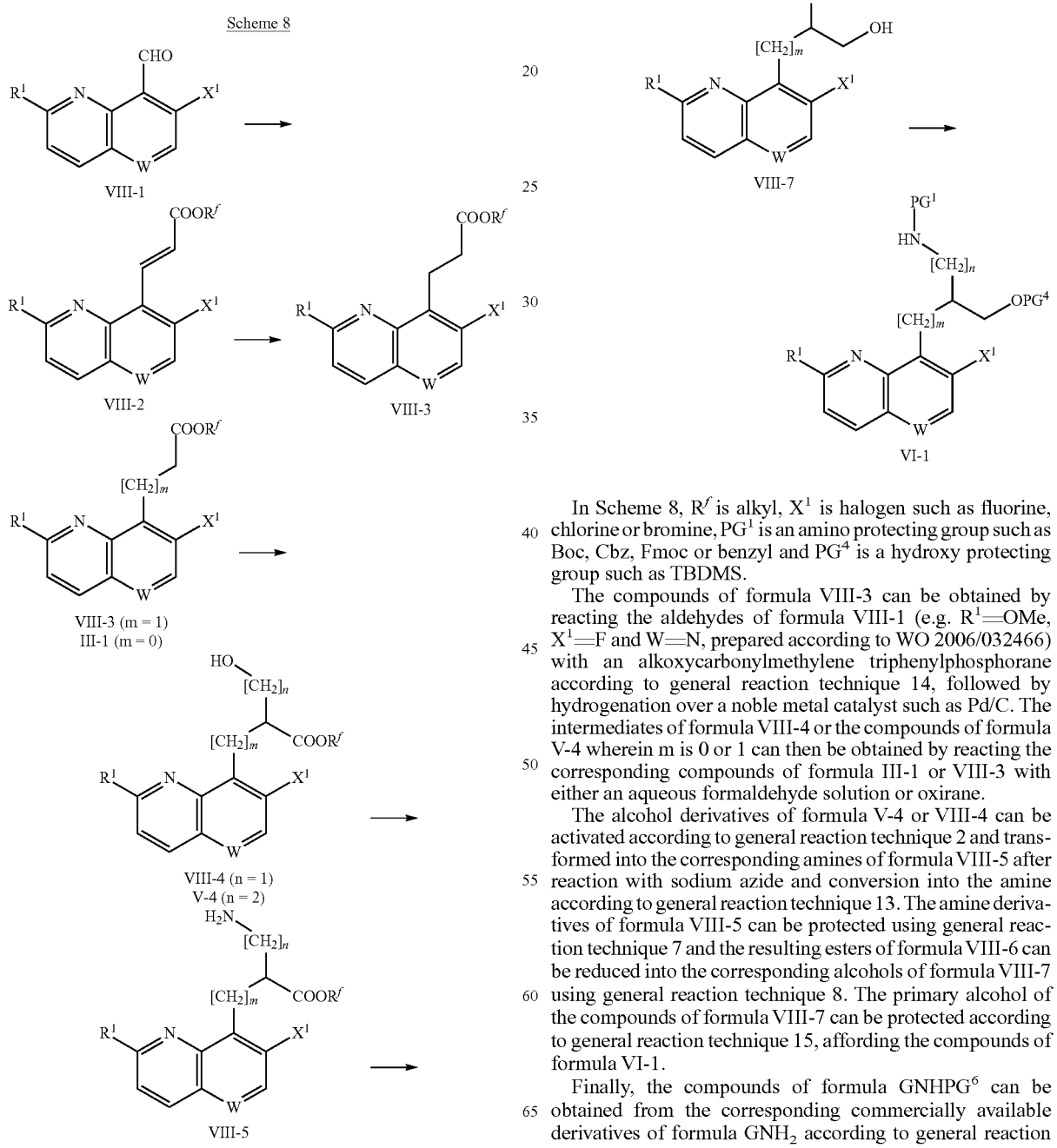

In Scheme 8, $R^f$ is alkyl, $X^1$ is halogen such as fluorine, chlorine or bromine, $PG^1$ is an amino protecting group such as Boc, Cbz, Fmoc or benzyl and $PG^4$ is a hydroxy protecting group such as TBDMS.

The compounds of formula VIII-3 can be obtained by reacting the aldehydes of formula VIII-1 (e.g. $R^1$=OMe, $X^1$=F and W=N, prepared according to WO 2006/032466) with an alkoxycarbonylmethylene triphenylphosphorane according to general reaction technique 14, followed by hydrogenation over a noble metal catalyst such as Pd/C. The intermediates of formula VIII-4 or the compounds of formula V-4 wherein m is 0 or 1 can then be obtained by reacting the corresponding compounds of formula III-1 or VIII-3 with either an aqueous formaldehyde solution or oxirane.

The alcohol derivatives of formula V-4 or VIII-4 can be activated according to general reaction technique 2 and transformed into the corresponding amines of formula VIII-5 after reaction with sodium azide and conversion into the amine according to general reaction technique 13. The amine derivatives of formula VIII-5 can be protected using general reaction technique 7 and the resulting esters of formula VIII-6 can be reduced into the corresponding alcohols of formula VIII-7 using general reaction technique 8. The primary alcohol of the compounds of formula VIII-7 can be protected according to general reaction technique 15, affording the compounds of formula VI-1.

Finally, the compounds of formula $GNHPG^6$ can be obtained from the corresponding commercially available derivatives of formula $GNH_2$ according to general reaction technique 7.

Particular embodiments of the invention are described in the following Examples, which serve to illustrate the invention in more detail without limiting its scope in any way.

EXAMPLES

All temperatures are stated in ° C. Compounds are characterized by $^1$H-NMR (300 MHz) (Varian Oxford); or by $^1$H-NMR (400 MHz) (Bruker Advance 400). Chemical shifts δ are given in ppm relative to the solvent used; multiplicities: s=singlet, d=doublet, t=triplet, q=quadruplet, p=pentuplet, hex=hexet, hept=heptet, m=multiplet, br.=broad, coupling constants are given in Hz. Alternatively compounds are characterized by LC-MS (Sciex API 2000 with Agilent 1100 Binary Pump and DAD, using RP-C18 based columns); by TLC (TLC-plates from Merck, Silica gel 60 $F_{254}$); or by melting point.

Compounds are purified by chromatography on Silica gel 60A. NH$_4$OH as used for CC is 25% aq. Racemates can be separated into their enantiomers as described before. Preferred conditions of chiral HPLC are: ChiralPak AD (4.6×250 mm, 5 μm) column, using an isocratic mixture (eg. at a ratio of 10/90) of eluent A (EtOH, in presence of diethylamine in an amount of eg. 0.1%) and eluent B (Hex), at rt, at a flow rate of eg. 0.8 mL/min.

General Procedures:

Procedure A: LAH Ester Reduction:

To a solution of ester (1 mmol) in THF (15 mL), cooled to 0° C., is added in one portion LAH (3.5 eq.). The mixture is stirred at the same temperature for 15 to 60 min. Water (0.46 mL) is carefully added, followed by 2M NaOH (0.80 mL) and water (0.80 mL). After stirring 5 min, Na$_2$SO$_4$ (1.2 g) is added and the mixture is stirred 15 min. The solids are filtered off and thoroughly washed with EA. The filtrate is concentrated to dryness under reduced pressure. The residue is then purified by CC.

Procedure B: Boc Deprotection:

The Boc protected amine (1 mmol) is dissolved in DCM (5 mL) and treated with Et$_3$SiH (optional; 0.2 mL, 1.1 eq.) and TFA (2 mL). The mixture is stirred at rt for 1 h, concentrated in vacuo and taken up in DCM/aq. NH$_4$OH. The org. layer is washed with water, dried over MgSO$_4$ and concentrated under reduced pressure.

Procedure C: Intramolecular Cyclisation:

To a solution of alcohol in THF (6 mL) is added KOtBu (2-4 eq.). The mixture is stirred in a sealed glass vial at 65° C. until completion of the reaction (ca. 1 h). After cooling to rt, water is added and the mixture is extracted with DCM. The aq. layer is basified with NH$_4$OH and extracted with DCM. The combined org. layers are concentrated to dryness under reduced pressure. The residue is then purified by CC.

Procedure D: Alkylation of Amines with Iodides:

A solution of amine (1 mmol), iodide (1 mmol) and DIPEA (1.1 mmol) in dry DMSO is heated to 70° C. until completion of the reaction (1-3 days). After cooling, water and EA are added and the phases are separated. The aq. layer is extracted two more times with EA and the combined org. layers are washed with water (3×) and brine, dried over MgSO$_4$ and concentrated under reduced pressure. The residue is then purified by CC.

Procedure E: Alkylation of Amines with Mesylates:

A solution of the amine (1.0-2.3 mmol), the mesylate (1 mmol) and DIPEA (1.1 mmol) in dry DMSO is heated to 70° C. until completion of the reaction (2-5 days). After cooling, water and EA are added and the phases are separated. The aq. layer is extracted two more times with EA and the combined org. layers are washed with water (3×) and brine, dried over MgSO$_4$ and concentrated under reduced pressure. The residue is then purified by CC.

Procedure F: Boc Protection:

To a solution of amine in DCM or THF are added TEA (1.5 eq.) and Boc$_2$O (1.05 eq.). The reaction is stirred at rt until completion of the reaction. The reaction mixture is then concentrated under reduced pressure.

Example 1

6-((R)-5-{[((RS)-6-methoxy-3,4-dihydro-2H-1-oxa-5-aza-phenanthren-3-ylmethyl)-amino]-methyl}-2-oxo-oxazolidin-3-yl)-4H-benzo[1,4]thiazin-3-one 1.i. rac-2-(tert-butoxycarbonylamino-methyl)-3-(7-fluoro-2-methoxy-quinolin-8-yl)-propionic acid ethyl ester To a solution of LiHMDS (1M, 20 mL), cooled to −78° C., was added dropwise a solution of 3-tert-butoxycarbonylamino-propionic acid ethyl ester (2.01 g, 9.26 mmol; prepared according to *Tetrahedron Lett*. (2003), 44(14), 2807) in THF (20 mL). The solution was stirred at the same temperature for 90 min. A solution of 8-bromomethyl-7-fluoro-2-methoxy-quinoline (2.5 g, 1 eq., prepared according to WO 2007/081597) in THF (10 mL) was quickly added and the reaction proceeded 2 h, keeping the internal temperature below −50° C. Water (100 mL) and EA (200 mL) were added. The two layers were separated and the aq. layer was extracted with EA. The combined org. layers were washed with brine, dried over Na$_2$SO$_4$, filtered and concentrated to dryness. The residue was purified by CC (Hept-EA 2-1) to afford the title intermediate as a pale yellow oil which solidified after standing at rt for one day (2.83 g, 75% yield). MS (ESI, m/z): 407.3 [M+H$^+$].

1.ii. rac-[3-(7-fluoro-2-methoxy-quinolin-8-yl)-2-hydroxymethyl-propyl]-carbamic acid tert-butyl ester Starting from intermediate 1.i and using procedure A, the title intermediate was obtained as a colourless oil (534 mg, 93% yield).

MS (ESI, m/z): 365.1 [M+H$^+$].

1.iii. rac-2-aminomethyl-3-(7-fluoro-2-methoxy-quinolin-8-yl)-propan-1-ol

Starting from intermediate 1.ii and using procedure B, the title intermediate was obtained as a colourless oil (311 mg, 52% yield).

MS (ESI, m/z): 265.3 [M+H$^+$].

1.iv. rac-C-(6-methoxy-3,4-dihydro-2H-1-oxa-5-aza-phenanthren-3-yl)-methylamine

Starting from intermediate 1.iii and using procedure C, the title intermediate was obtained as a colourless oil (120 mg, 47% yield).

MS (ESI, m/z): 245.3 [M+H$^+$].

1.v. 6-((S)-3-chloro-2-hydroxy-propylamino)-4H-benzo[1,4]thiazin-3-one

A suspension of 6-amino-4H-benzo[1,4]thiazin-3-one (18.0 g, 100 mmol; commercial) and Ca(OTf)$_2$ (0.5 eq.) in MeCN (800 mL) was heated at 50° for 1 h. (S)-epichlorohydrin (18.5 g, 200 mmol) was added and the mixture was stirred at rt for 72 h and at 45° C. for 24 h. The volatiles were removed under reduced pressure. After aqueous workup and extraction with EA, the title intermediate crystallized from EA to afford a beige solid (17.38 g, 64% yield).

MS (ESI, m/z): 273.2 [M+H$^+$].

1.vi. 6-((S)-5-chloromethyl-2-oxo-oxazolidin-3-yl)-4H-benzo[1,4]thiazin-3-one

A solution of intermediate 1.v (17.38 g, 63.7 mmol) in THF (300 mL) was treated with CDI (1.2 eq.) and stirred at rt for 30 min and at 50° C. for 5 h. The mixture was concentrated, diluted with EA and washed with water and brine, dried over MgSO$_4$ and concentrated. The residue was purified by CC (EA/Hept 2:1, EA) to afford the title intermediate as a pale yellow solid (14.0 g, 74% yield).

MS (ESI, m/z): 299.1 [M+H$^+$].

1.vii. 6-((S)-5-iodomethyl-2-oxo-oxazolidin-3-yl)-4H-benzo[1,4]thiazin-3-one

A mixture of intermediate 1.vi (14.0 g, 46.9 mmol) and NaI (3 eq.) in 2-butanone (150 mL) was heated at 85° C. for 2 days. After cooling to rt, the mixture was diluted with 10% Na$_2$S$_2$O$_3$ (300 mL) and ether/EA (100 mL). The mixture was vigorously stirred for 10 min and filtered. The solids were thoroughly washed with water and ether and dried at HV to afford a pale beige solid. The phases of the combined filtrates were separated and the org. phase washed with brine, dried over MgSO$_4$ and concentrated to afford a pale beige solid. The solids of both processes were combined to afford the title intermediate as a pale beige solid (15.0 g, 82% yield).

MS (ESI, m/z): 391.4 [M+H$^+$].

1.viii. 6-((R)-5-{[((RS)-6-methoxy-3,4-dihydro-2H-1-oxa-5-aza-phenanthren-3-ylmethyl)-amino]-methyl}-2-oxo-oxazolidin-3-yl)-4H-benzo[1,4]thiazin-3-one Starting from intermediates 1.iv and 1.vii and using procedure D, the title compound was obtained as a colourless solid (40 mg, 36% yield).

$^1$H NMR (CDCl$_3$) δ: 8.39 (s, 1H), 7.85 (d, J=8.8 Hz, 1H), 7.43 (m, 2H), 7.27 (m, 1H), 6.93 (m, 2H), 6.74 (d, J=8.8 Hz, 1H), 4.77 (m, 1H), 4.34 (m, 1H), 3.95 (m, 6H), 3.60-3.30 (m, 5H), 2.91 (m, 4H), 2.26 (m, 1H).

MS (ESI, m/z): 506.9 [M+H$^+$].

Example 2

6-((R)-5-{[((RS)-6-methoxy-3,4-dihydro-2H-1-oxa-5-aza-phenanthren-3-ylmethyl)-amino]-methyl}-2-oxo-oxazolidin-3-yl)-4H-benzo[1,4]oxazin-3-one 2.i. 6-[(S)-3-(tert-butyl-dimethyl-silanyloxy)-2-hydroxy-propylamino]-4H-benzo[1,4]oxazin-3-one To a solution of tert-butyl-dimethyl-((S)-1-oxiranylmethoxy)-silane (commercial; 13.0 g, 69 mmol) in MeCN (220 mL) was added LiClO$_4$ (22 g, 207 mmol). 6-amino-4H-benzo[1,4]oxazin-3-one (commercial; 11.45 g, 64 mmol) was added and the mixture was stirred at 50° C. for 6 h. The solvent was removed in vacuo and the residue was purified by CC (DCM/MeOH/NH$_4$OH 1000/25/2 to 1000/100/2) to afford the title intermediate as a pale brown foam (11.16 g, 44% yield).

MS (ESI, m/z): 353.3 [M+H$^+$].

2.ii. 6-[(S)-5-(tert-butyl-dimethyl-silanyloxymethyl)-2-oxo-oxazolidin-3-yl]-4H-benzo[1,4]oxazin-3-one A solution of intermediate 2.i (11.16 g, 30 mmol) and CDI (5.57 g, 33 mmol) in THF (130 mL) was heated at 50° C. for 2 h; the mixture was concentrated in vacuo and partitioned between EA and water. Some crystallized product was filtered and washed with H$_2$O and EA to afford 5.21 g of solid. The org. layer was washed with brine, dried over MgSO$_4$ and concentrated under reduced pressure. The residue was purified by purified by CC (DCM/MeOH 1000:50:4) to give additional 2.28 g of product as a colourless solid (total: 7.49 g, 63% yield).

MS (ESI, m/z): 379.2 [M+H$^+$].

2.iii. 6-((S)-5-hydroxymethyl-2-oxo-oxazolidin-3-yl)-4H-benzo[1,4]oxazin-3-one

A suspension of intermediate 2.ii (11.49 g, 29.1 mmol) in THF (30 mL) was treated with TBAF (1M in THF, 29.1 mL). The yellow solution was stirred at 0° C. for 3 h and then partitioned between water and EA. Some crystallized product was filtered and washed with H$_2$O and EA to give 6.49 g of an off-white solid. The aq. phase was extracted with EA (3×). The combined org. layers were washed with brine, dried over MgSO$_4$, filtered and concentrated under reduced pressure. The crude product was triturated with EA to give 1.23 g of an off-white solid (total: 7.72 g, 95% yield).

MS (ESI, m/z): 265.5 [M+H$^+$].

2.iv. Methanesulfonic acid (S)-2-oxo-3-(3-oxo-3,4-dihydro-2H-benzo[1,4]oxazin-6-yl)-oxazolidin-5-ylmethyl ester A suspension of intermediate 2.iii (5.45 g, 20.6 mmol) in anhydrous DCM (110 mL) was treated with DIPEA (3.5 eq.) and the mixture was cooled to 0° C. Ms$_2$O (1.5 eq.) was added dropwise. The resulting mixture was stirred at 0° C. for 15 min. Water was added and stirring was continued for 15 min at rt. The precipitated product was filtered, washed with water and DCM, and triturated with DCM/MeOH/NH$_4$OH (1000/25/2) to give the title intermediate as a colourless solid (3.75 g, 53% yield).

$^1$H NMR (DMSO-d6) δ: 10.72 (s, 1H), 7.29 (dd, J=2.1, 0.6 Hz, 1H), 6.94 (m, 2H), 4.95 (m, 1H), 4.52 (s, 2H), 4.49 (m, 2H), 4.11 (t, J=9.1 Hz, 1H), 3.73 (m, 3.23 (s, 3H).

MS (ESI, m/z): 343.3 [M+H$^+$].

2.v. 6-((R)-5-{[((RS)-6-methoxy-3,4-dihydro-2H-1-oxa-5-aza-phenanthren-3-ylmethyl)-amino]-methyl}-2-oxo-oxazolidin-3-yl)-4H-benzo[1,4]oxazin-3-one Starting from intermediates 1.iv and 2.iv and using procedure E, the title compound was obtained as a colourless solid (9 mg, 11% yield).

MS (ESI, m/z): 490.9 [M+H$^+$].

Example 3

6-((R)-5-{[((RS)-6-methoxy-3,4-dihydro-2H-1-oxa-5,9-diaza-phenanthren-3-ylmethyl)-amino]-methyl}-2-oxo-oxazolidin-3-yl)-4H-benzo[1,4]oxazin-3-one

3.i. (3-fluoro-6-methoxy-[1.5]naphthyridin-4-yl)-methanol

To an ice-chilled suspension of 3-fluoro-6-methoxy-[1.5] naphthyridine-4-carbaldehyde (5 g, 24.25 mmol; prepared as in WO 2006/032466) in MeOH (180 mL) was added NaBH$_4$ (1.03 g, 26.68 mmol, 1.1 eq.) in one portion. After 30 min, the reaction mixture was warmed to rt. Water (180 mL) was added and the volatiles were removed under reduced pressure. The residue was filtered off and washed with water. The aq. filtrate was extracted twice with EA (2×100 mL). The combined org. layers were washed with brine (120 mL), dried over Na$_2$SO$_4$, filtered and evaporated under reduced pressure to afford a yellow solid. The residue was purified by CC (Hept-EA 1:1) to give the title intermediate as a pale yellow solid (4.01 g, 79% yield).
MS (ESI, m/z): 209.4 [M+H$^+$].

3.ii. 8-bromomethyl-7-fluoro-2-methoxy-[1.5]naphthyridine

To a solution of intermediate 3.i (4.01 g, 19.2 mmol) in DMF (28.5 mL) was added at rt PBr$_3$ (2 mL). After stirring the reaction at rt for 80 min, water (95 mL) and sat. NaHCO$_3$ (ca. 45 mL) were added until no gas evolution was observed any longer. The solid that formed was filtered off and washed with water. The solid was taken up in EA (250 mL), dried over MgSO$_4$, and the solution was directly filtered through a pad of silica gel. The filtrate was concentrated to dryness to give the title intermediate as a pale yellow solid (4.60 g, 88% yield).
MS (ESI, m/z): 270.9 [M+H$^+$].

3.iii. rac-2-(tert-butoxycarbonylamino-methyl)-3-(3-fluoro-6-methoxy-[1,5]naphthyridin-4-yl)-propionic acid ethyl ester To a solution of LiHMDS (1M, 17 mL), cooled to −78° C., was added dropwise a solution of 3-tert-butoxycarbonylamino-propionic acid ethyl ester (1.7 g, 7.8 mmol; prepared according to *Tetrahedron Lett*. (2003), 44(14), 2807) in THF (20 mL). The solution was stirred at the same temperature for 90 min. A solution of intermediate 3.ii (2.1 g, 7.8 mmol) in THF (10 mL) was quickly added and the reaction proceeded 2 h, keeping the internal temperature below −50° C. Water (100 mL) and EA (200 mL) were added. The two layers were decanted and the aq. layer was extracted with EA. The combined org. layers were washed with brine, dried over MgSO$_4$, filtered and concentrated to dryness. The residue was purified by CC (Hept-EA 2:1) to afford the title intermediate as a pale yellow oil (2.38 g, 75% yield).
MS (ESI, m/z): 408.6 [M+H$^+$].

3.iv. rac-[3-(3-fluoro-6-methoxy-[1,5]naphthyridin-4-yl)-2-hydroxymethyl-propyl]-carbamic acid tert-butyl ester Starting from intermediate 3.iii and using procedure A, the title compound was obtained as a pale yellow oil (1.59 g, 74% yield).
MS (ESI, m/z): 366.2 [M+H$^+$].

3.v. rac-aminomethyl-3-(3-fluoro-6-methoxy-[1,5]naphthyridin-4-yl)-propan-1-ol Starting from intermediate 3.iv and using procedure B, the title compound was obtained as a yellow oil (688 mg, 100% yield).
MS (ESI, m/z): 266.2 [M+H$^+$].

3.vi. rac-C-(6-methoxy-3,4-dihydro-2H-1-oxa-5,9-diaza-phenanthren-3-yl)-methylamine Starting from intermediate 3.v and using procedure C, the title compound was obtained as a yellow oil (150 mg, 52% yield).
MS (ESI, m/z): 246.3 [M+H$^+$].

3.vii. 6-((R)-5-{[((RS)-6-methoxy-3,4-dihydro-2H-1-oxa-5,9-diaza-phenanthren-3-ylmethyl)-amino]-methyl}-2-oxo-oxazolidin-3-yl)-4H-benzo[1,4]oxazin-3-one Starting from intermediates 3.vi and 2.iv and using procedure E, the title compound was obtained as a colourless solid (47 mg, 26% yield).
MS (ESI, m/z): 492.0 [M+H$^+$].

Example 4

6-((R)-5-{[((RS)-6-methoxy-3,4-dihydro-2H-1-oxa-5,9-diaza-phenanthren-3-ylmethyl)-amino]-methyl}-2-oxo-oxazolidin-3-yl)-4H-benzo[1,4]thiazin-3-one Starting from intermediates 3.vi and 1.vii and using procedure D, the title compound was obtained as a pale yellow foam (31 mg, 25% yield).
$^1$H NMR (CDCl$_3$) δ: 8.40 (s, 1H), 8.24 (s, 1H), 8.10 (dd, J=8.8, 0.9 Hz, 1H), 7.42 (d, J=2.3 Hz, 1H), 7.28 (m, 1H), 6.93 (m, 2H), 4.78 (m, 1H), 4.38 (m, 1H), 4.06 (m, 5H), 3.86 (m, 1H), 3.42 (s, 2H), 3.32 (m, 1H), 3.08 (m, 1H), 2.84 (m, 4H), 2.29 (m, 1H). MS (ESI, m/z): 508.0 [M+H$^+$].

Example 5

6-((R)-5-{[((RS)-6-methoxy-1,2,3,4-tetrahydro-1,5,9-triaza-phenanthren-3-ylmethyl)-amino]-methyl}-2-oxo-oxazolidin-3-yl)-4H-benzo[1,4]thiazin-3-one

5.i. rac-(6-methoxy-1,2,3,4-tetrahydro-1,5,9-triaza-phenanthren-3-yl)-methanol To a solution of intermediate 3.v (298 mg, 1.12 mmol) in NMP (8 mL) was added DIPEA (1.2 eq.). The mixture was stirred in a sealed glass vial at 90° C. for 6 h. After cooling to rt, water was added and the mixture was extracted with EA (2×). The org. layer was washed several times with water and once with brine, dried over MgSO$_4$ and concentrated. The residue was purified by CC (DCM-MeOH—NH$_4$OH 1000:100:8) to afford the title intermediate as a colourless foam (84 mg, 30% yield).
MS (ESI, m/z): 246.1 [M+H$^+$].

5.ii. rac-C-(6-methoxy-1,2,3,4-tetrahydro-1,5,9-triaza-phenanthren-3-yl)-methylamine PPh$_3$ (143 mg, 0.54 mmol) was dissolved in THF (2 mL) and then cooled to 0° C. DIAD (116 mg, 0.54 mmol) was then added via a syringe at 0° C. After the solution was stirred for 15 min (yellow suspension), a solution of intermediate 5.i (88 mg, 0.36 mmol) in THF (1 mL) was slowly added, followed immediately by the addition of DPPA (151 mg, 0.54 mmol). The reaction mixture was allowed to warm to rt and stirred for 4 h. The mixture was concentrated and the residue was filtered over a short pad of silica gel using EA as eluent. The solution was concentrated and the resulting crude azide intermediate was dissolved in THF (1.5 mL). To this solution was added PPh$_3$ (194 mg, 0.74 mmol) and water (0.67 mL, 10 eq.). The mixture was heated at 50° C. for 1 h. The reaction mixture was concentrated and the residue was taken in DCM and extracted with 10% citric acid (2×). The comb. aq. layers were basified with NH$_4$OH and then extracted with 9:1 DCM-MeOH (3×). The comb. org. layers were concentrated and the residue was purified by CC (DCM-MeOH—NH$_4$OH 1000:100:8 to 1000: 200:16) to afford the title intermediate as a yellow solid (31 mg, 35% yield).

MS (ESI, m/z): 245.2 [M+H$^+$].

5.iii. 6-((R)-5-{[((RS)-6-methoxy-1,2,3,4-tetrahydro-1,5,9-triaza-phenanthren-3-ylmethyl)-amino]-methyl}-2-oxo-oxazolidin-3-yl)-4H-benzo[1,4]thiazin-3-one Starting from intermediates 5.ii and 1.vii and using procedure D, the title compound was obtained as a pale yellow foam (14 mg, 21% yield).

MS (ESI, m/z): 507.1 [M+H$^+$].

Example 6

6-((R)-5-{[2-((RS)-2-methoxy-8,9-dihydro-furo[2,3-h]quinolin-9-yl)-ethylamino]-methyl}-2-oxo-oxazolidin-3-yl)-4H-benzo[1,4]thiazin-3-one

6.i. rac-3-cyano-2-(7-fluoro-2-methoxy-quinolin-8-yl)-propionic acid methyl ester To a solution of (7-fluoro-2-methoxy-quinolin-8-yl)-acetic acid methyl ester (1.0 g, 4.0 mmol; prepared as in WO 2007/081597) in THF (10 mL) cooled to −78° C. was added LiHMDS (1M, 4.43 mL, 1.2 eq.) dropwise over 15 min. The resulting orange mixture was stirred at −78° C. for 2 h. Bromoacetonitrile (1.5 eq.) was added dropwise over 20 min and stirring was continued at −78° C. for an additional 2 h. The reaction was quenched with water and extracted with EA (3×). The combined org. phases were washed with brine, dried over MgSO$_4$, filtered and concentrated. The residue was purified by CC (Hept/EA 2:1 to 1:1) to afford the title intermediate as a colourless solid (953 mg, 82% yield). MS (ESI, m/z): 289.4 [M+H$^+$].

6.ii. rac-4-amino-2-(7-fluoro-2-methoxy-quinolin-8-yl)-butan-1-ol

To a solution of AlCl$_3$ (967 mg, 7.25 mmol) in Et$_2$O (50 mL) cooled to −78° C. was added LAH (1M in THF, 7.25 mL) within 10 min. After stirring for 15 min at −78° C., a suspension of intermediate 6.i (950 mg, 3.30 mmol) in Et$_2$O (40 mL) was added within 15 min. The resulting suspension was then stirred at rt for 4 h, cooled to 0° C., and quenched with sat. Na$_2$SO$_4$. The mixture was basified with NH$_4$OH and extracted with EA (3×). The combined org. phases were dried over Na$_2$SO$_4$, filtered and concentrated to afford the title intermediate as a yellow oil (870 mg, 100% yield).

MS (ESI, m/z): 265.3 [M+H$^+$].

6.iii. rac-2-(2-methoxy-8,9-dihydro-furo[2,3-h]quinolin-9-yl)-ethylamine

Starting from intermediate 6.ii and using procedure C, the title compound was obtained as a yellow foam (236 mg, 96% yield).

MS (ESI, m/z): 245.1 [M+H$^+$].

6.iv. 6-((R)-5-{[2-((RS)-2-methoxy-8,9-dihydro-furo[2,3-h]quinolin-9-yl)-ethylamino]-methyl}-2-oxo-oxazolidin-3-yl)-4H-benzo[1,4]thiazin-3-one Starting from intermediates 6.iii and 1.vii and using procedure D, the title compound was obtained as an off-white foam (18 mg, 8% yield).

MS (ESI, m/z): 507.0 [M+H$^+$].

Example 7

6-((R)-5-{[2-((RS)-2-methoxy-8,9-dihydro-furo[2,3-h]quinolin-9-yl)-ethylamino]-methyl}-2-oxo-oxazolidin-3-yl)-4H-benzo[1,4]oxazin-3-one Starting from intermediates 6.iii and 2.iv and using procedure E, the title compound was obtained as a pale yellow foam (14 mg, 6% yield).

MS (ESI, m/z): 490.9 [M+H$^+$].

Example 8

6-((R)-5-{[((RS)-2-methoxy-8,9-dihydro-furo[2,3-h]quinolin-9-ylmethyl)-amino]-methyl}-2-oxo-oxazolidin-3-yl)-4H-benzo[1,4]thiazin-3-one

8.i. rac-3-(1,3-dioxo-1,3-dihydro-isoindol-2-yl)-2-(7-fluoro-2-methoxy-quinolin-8-yl)-propionic acid methyl ester To a solution of LiHMDS (1M in THF, 9.6 mL) was added at −78° C. a solution of (7-fluoro-2-methoxy-quinolin-8-yl)-acetic acid methyl ester (2.0 g, 8.0 mmol; prepared as in WO 2007/081597) in THF (16 mL) over 10 min. After stirring the resulting orange mixture for 1 h at −78° C., a solution of N-(bromomethyl)phthalimide (1.2 eq.) in THF (16 mL) was added dropwise over 10 min. The mixture was stirred 1 h at −78° C. and then at rt overnight. The yellow solution was quenched with 1N HCl (80 mL) and then extracted with DCM. The combined org layers were washed with water, dried over MgSO$_4$, concentrated and purified by CC (Hept/EA 1:1) to give 1.89 g of a yellow solid which was recrystallized from EA/MeOH/NH$_4$OH (90:10:1) to afford the title intermediate as a colourless solid (924 mg, 28% yield).

MS (ESI, m/z): 409.3 [M+H$^+$].

8.ii. rac-3-tert-butoxycarbonylamino-2-(7-fluoro-2-methoxy-quinolin-8-yl)-propionic acid methyl ester To a suspension of intermediate 8.i (774 mg, 1.90 mmol) in EtOH (10 mL) was added dropwise hydrazine monohydrate (0.46 mL, 5 eq.) at rt. The mixture was stirred for 2 h at rt. The solvent was removed under reduced pressure and the colourless residue taken up in EA and citric acid 10%. The layers were separated and the aq. phase was washed with EA. The org. layers were discarded. The product containing aq. phase was rebasified with NH$_4$OH and extracted twice with DCM.

The combined DCM phases were dried over MgSO$_4$ and concentrated to afford a pale yellow solid (526 mg). The thus obtained free amine was Boc protected according to procedure F to afford the title intermediate as a pale yellow foam (656 mg, 92% yield).

MS (ESI, m/z): 379.1 [M+H$^+$].

8.iii. rac-[2-(7-fluoro-2-methoxy-quinolin-8-yl)-3-hydroxy-propyl]-carbamic acid tert-butyl ester Starting from intermediate 8.ii and using procedure A, the title compound was obtained as a pale yellow foam (675 mg, 81% yield).

MS (ESI, m/z): 351.3 [M+H$^+$].

8.iv. rac-3-amino-2-(7-fluoro-2-methoxy-quinolin-8-yl)-propan-1-ol

Starting from intermediate 8.iii and using procedure B, the title compound was obtained as a pale yellow oil (266 mg, 92% yield).

MS (ESI, m/z): 251.1 [M+H$^+$].

8.v. rac-C-(2-methoxy-8,9-dihydro-furo[2,3-h]quinolin-9-yl)-methylamine

Starting from intermediate 8.iv and using procedure C, the title compound was obtained as a yellow oil (59 mg, 24% yield).

MS (ESI, m/z): 231.4 [M+H$^+$].

8.vi. 6-((R)-5-{[((RS)-2-methoxy-8,9-dihydro-furo[2,3-h]quinolin-9-ylmethyl)-amino]-methyl}-2-oxo-oxazolidin-3-yl)-4H-benzo[1,4]thiazin-3-one Starting from intermediates 8.v and 1.vii and using procedure D, the title compound was obtained as an off-white foam (9 mg, 15% yield).

MS (ESI, m/z): 492.9 [M+H$^+$].

Example 9

6-((R)-5-{[2-((RS)-8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]thiazin-3-one

9.i. rac-3-cyano-2-(3-fluoro-6-methoxy-[1,5]naphthyridin-4-yl)-propionic acid ethyl ester LiRMDS in THF (1M; 12.5 mL) was added at −78° C. during 15 min to a solution of (3-fluoro-6-methoxy-[1,5]naphthyridin-4-yl)-acetic acid ethyl ester (3.00 g; prepared in analogy to the corresponding methyl ester described in WO 2007/122258) in THF (30 mL). The resulting orange mixture was stirred at −78° C. for 2 h. Bromoacetonitrile (1.13 mL) was added dropwise and the reaction mixture was further stirred at −78° C. for 2 h. The reaction mixture was treated with water and extracted with EA. The combined org. phases were washed with brine, dried over MgSO$_4$, filtered and concentrated. The crude product was purified by CC (Hept/EA 2:1 to 1:1) affording a yellow oil (3.09 g; 89.7% yield).

MS (ESI, m/z): 304.4 [M+H$^+$].

9.ii. rac-4-amino-2-(3-fluoro-6-methoxy-[1,5]naphthyridin-4-yl)-butan-1-ol

A solution of LAH in THF (1M; 22 mL) was added dropwise at −78° C. to a solution of AlCl$_3$ in Et$_2$O (100 mL). After stirring for 15 min a solution of intermediate 9.i (3.0 g) in Et$_2$O (140 mL) was added dropwise. After further stirring at −78° C. for 1 h, the suspension was allowed to reach 0° C. over 5 h. The reaction mixture was sequentially treated with a sat. aq. Na$_2$SO$_4$ solution, water and aq. NH$_4$OH before extraction with EA. The org. phase was dried over Na$_2$SO$_4$, filtered and concentrated. The crude product was purified by CC (DCM/MeOH/NH$_4$OH 1000:100:8 to 1000:200:16), affording a yellow oil (1.0 g; 38% yield).

MS (ESI, m/z): 266.3 [M+H$^+$].

9.iii. rac-2-(8-methoxy-1,2-dihydro-3-oxa-5,9-diaza-cyclopenta[a]naphthalen-1-yl)-ethylamine tBuOK (840 mg) was added to a solution of intermediate 9.ii (994 mg) in THF (16 mL). The mixture was stirred in a sealed glass vial at 70° C. for 10 min. After cooling to rt, water was added and the mixture was extracted with DCM (3×). The combined org. layers were dried over MgSO$_4$ and concentrated to dryness. The residue was purified by CC (DCM/MeOH/NH$_4$OH 1000:100:8), affording a yellow oil (330 mg; 36.4% yield).

MS (ESI, m/z): 246.3 [M+H$^+$].

9.iv. 6-((R)-5-{[2-((RS)-8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]thiazin-3-one Starting from intermediates 1.vii (74.2 mg) and 9.iii (45 mg) and using procedure D, the title compound was obtained as a yellow foam (18 mg; 21% yield).

MS (ESI, m/z): 508.2 [M+H$^+$].

Example 10

6-((R)-5-{[2-((RS)-8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]oxazin-3-one Starting from intermediates 2.iv (55.8 mg) and 9.iii (40 mg) and using procedure D, the title compound was obtained as a light brown foam (3 mg; 2% yield).

MS (ESI, m/z): 492.0 [M+H$^+$].

Example 11

(R)-3-(3-fluoro-4-methyl-phenyl)-5-{[2-((RS)-8-methoxy-1,2-dihydro-3-oxa-5,9-diaza-cyclopenta[a]naphthalen-1-yl)-ethylamino]-methyl}-oxazolidin-2-one Starting from intermediate 9.iii (40 mg) and (5S)-3-(3-fluoro-4-methylphenyl)-5-(iodomethyl)-2-oxazolidinone (56 mg; prepared according to WO 2008/126034) and proceeding in analogy to Example 10, the title compound was obtained as a yellow oil (1 mg; 1% yield).

MS (ESI, m/z): 453.1 [M+H$^+$].

Example 12

6-((S)-5-{[2-((RS)-8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]thiazin-3-one Starting from intermediate 9.iii (40 mg) and 6-((R)-5-iodomethyl-2-oxo-oxazolidin-3-yl)-4H-benzo[1,4]thiazin-3- one (63 mg; prepared according to WO 2008/126034) and proceeding in analogy to Example 10, the title compound was obtained as a light yellow solid (12 mg; 15% yield).
MS (ESI, m/z): 508.0 [M+H$^+$].

Example 13

6-((R)-5-{2-[2-((RS)-8-methoxy-1,2-dihydro-3-oxa-5,9-diaza-cyclopenta[a]naphthalen-1-yl)-ethylamino]-ethyl}-2-oxo-oxazolidin-3-yl)-4H-benzo[1,4]thiazin-3-one 13.i. 6-[(R)-4-(tert-butyl-dimethyl-silanyloxy)-2-hydroxy-butylamino]-4H-benzo[1,4]thiazin-3-one A solution of (2R)-2-[2-[[tert-butyldimethylsilyl]oxy]ethyl]-oxirane (12.0 g; prepared according to WO 2007/144423) and 6-amino-4H-benzo[1,4]thiazin-3-one (10.7 g; commercial) in EtOH/water (9:1) was heated to 80° C. for 2 days. The solvents were removed under reduced pressure and the residue was triturated in ether/MeOH and filtered. The filtrate was evaporated under reduced pressure, affording a brown oil (18.8 g; 83% yield).
MS (ESI, m/z): 383.2 [M+H$^+$].

13.ii. 6-{(R)-5-[2-(tert-butyl-dimethyl-silanyloxy)-ethyl]-2-oxo-oxazolidin-3-yl}-4H-benzo[1,4]thiazin-3-one Starting from intermediate 13.i (23.5 g) and CDI (7.97 g) and proceeding in analogy to Example 1, step 1.vi, the title compound was obtained as a colourless solid (8.40 g; 42% yield).
MS (ESI, m/z): 409.3 [M+H$^+$].

13.iii. 6-[(R)-5-(2-hydroxy-ethyl)-2-oxo-oxazolidin-3-yl]-4H-benzo[1,4]thiazin-3-one Starting from intermediate 13.ii (8.4 g) and proceeding in analogy to Example 2, step 2.iii, the title compound was obtained as a colourless solid (4.79 g; 79% yield).
MS (ESI, m/z): 295.5 [M+H$^+$].

13.iv. Methanesulfonic acid 2-[(R)-2-oxo-3-(3-oxo-3,4-dihydro-2H-benzo[1,4]thiazin-6-yl)-oxazolidin-5-yl]-ethyl ester Starting from intermediate 13.iii (4.7 g) and proceeding in analogy to Example 2, step 2.iv, the title compound was obtained as a colourless solid (5.80 g; 98% yield).
MS (ESI, m/z): 373.4 [M+H$^+$].

13.v. 6-((R)-5-{2-[2-((RS)-8-methoxy-1,2-dihydro-3-oxa-5,9-diaza-cyclopenta[a]naphthalen-1-yl)-ethylamino]-ethyl}-2-oxo-oxazolidin-3-yl)-4H-benzo[1,4]thiazin-3-one Starting from intermediates 13.iv and 9.iii and using procedure E, the title compound was obtained as a light yellow solid (19 mg, 22% yield).
$^1$H NMR (CDCl$_3$) δ: 8.80 (s, 1H), 8.44 (s, 1H), 8.07 (d, J=9.1 Hz, 1H), 7.38 (m, 1H), 7.27 (m, 1H), 6.98 (m, 1H), 6.87 (d, J=8.8 Hz, 1H), 5.09 (m, 1H), 4.80 (m, 1H), 4.14 (m, 1H), 4.03 (m, 3H), 3.67 (m, 1H), 3.48 (m, 1H), 3.38 (m, 1H), 3.23 (d, J=9.7 Hz, 1H), 2.95 (m, 2H), 2.49 (m, 4H), 2.13 (m, 2H), 1.90 (m, 1H).
MS (ESI, m/z): 522.2 [M+H$^+$].

Example 14

6-((R)-5-{2-[((RS)-8-methoxy-1,2-dihydro-3-oxa-5,9-diaza-cyclopenta[a]naphthalen-1-ylmethyl)-amino]-ethyl}-2-oxo-oxazolidin-3-yl)-4H-benzo[1,4]thiazin-3-one 14.i. rac-3-(1,3-dioxo-1,3-dihydro-isoindol-2-yl)-2-(3-fluoro-6-methoxy-[1,5]naphthyridin-4-yl)-propionic acid ethyl ester A solution of (3-fluoro-6-methoxy-[1,5]naphthyridin-4-yl)-acetic acid ethyl ester (6.78 g; prepared in analogy to the corresponding methyl ester described in WO 2007/122258) in THF (30 mL) was added dropwise at −78° C. to a solution of LiHMDS (31 mL; 1M in THF) diluted in THF (20 mL). After stirring for 1 h at −78° C. a solution of N-(bromomethyl) phthalimide (7.40 g) in THF (30 mL) was added dropwise and the mixture was stirred for an additional 1 h at −78° C. and then overnight at rt. The yellow solution was quenched with 1N HCl (280 mL) and extracted with DCM. The combined org. layers were washed with H$_2$O, dried over MgSO$_4$, concentrated and purified by CC (Hept/EA 1:1), affording a light yellow foam (5.49 g; 51% yield).
MS (ESI, m/z): 424.2 [M+H$^+$].

14.ii. rac-3-amino-2-(3-fluoro-6-methoxy-[1,5]naphthyridin-4-yl)-propionic acid ethyl ester Hydrazine monohydrate (3.15 mL) was added dropwise at rt to a suspension of the intermediate 14.i (5.5 g) in EtOH (90 mL) and the mixture was further stirred for 2 h at rt. The solvent was removed under reduced pressure and the residue was taken up in EA and aq. citric acid (10%). The aq. layer was washed with EA, treated with aq. NH$_4$OH (28%) and extracted twice with DCM. The combined DCM phases were dried over MgSO$_4$ and concentrated under reduced pressure, affording a yellow oil (2.59 g; 68% yield).
MS (ESI, m/z): 294.2 [M+H$^+$].

14.iii. rac-3-tert-butoxycarbonylamino-2-(3-fluoro-6-methoxy-[1,5]naphthyridin-4-yl)-propionic acid ethyl ester Starting from intermediate 14.ii (2.59 g) using procedure F, the title compound was obtained as an orange oil (2.91 g, 97% yield).
MS (ESI, m/z): 394.2 [M+H$^+$].

14.iv. rac-[2-(3-fhtoro-6-methoxy-[1,5]naphthyridin-4-yl)-3-hydroxy-propyl]-carbamic acid tert-butyl ester Starting from intermediate 14.iii (2.23 g) using procedure A, the title compound was obtained as a yellow foam (2.3 g, quantitative yield).
MS (ESI, m/z): 352.2 [M+H$^+$].

14.v. rac-3-amino-2-(3-fluoro-6-methoxy-[1,5]naphthyridin-4-yl)-propan-1-ol

Starting from intermediate 14.iv (850 mg) using procedure B, the title compound was obtained as an orange gum (644 mg; quantitative yield).
MS (ESI, m/z): 252.2 [M+H$^+$].

14. vi. rac-C-(8-methoxy-1,2-dihydro-3-oxa-5,9-diaza-cyclopenta[a]naphthalen-1-yl)-methylamine Starting from intermediate 14.v (200 mg) and using procedure C, the title compound was obtained as a yellow solid (61 mg, 33% yield).
MS (ESI, m/z): 232.3 [M+H$^+$].

14. vii. 6-((R)-5-{2-[((RS)-8-methoxy-3-oxa-5,9-diaza-cyclopenta[a]naphthalen-1-ylmethyl)-amino]-ethyl}-2-oxo-oxazolidin-3-yl)-4H-benzo[1,4]thiazin-3-one Starting from intermediates 14.vi (20 mg) and 13.iv (32 mg) and using procedure E, the title compound was obtained as a light yellow solid (10 mg, 23% yield).
MS (ESI, m/z): 508.0 [M+H$^+$].

Example 15

6-((S)-5-{2-[((RS)-8-methoxy-1,2-dihydro-3-oxa-5,9-diaza-cyclopenta[a]naphthalen-1-ylmethyl)-amino]-ethyl}-2-oxo-oxazolidin-3-yl)-4H-benzo[1,4]thiazin-3-one

15.i. Methanesulfonic acid 2-[(S)-2-oxo-3-(3-oxo-3,4-dihydro-2H-benzo[1,4]thiazin-6-yl)-oxazolidin-5-yl]-ethyl ester Starting from (2S)-2-[2-[[tert-butyldimethylsilyl]oxy]ethyl]-oxirane (prepared according to *J. Org. Chem.* (1992), 57, 353-358) and proceeding in analogy to Example 13, steps 13.i to 13.iv, the title compound was obtained as an off-white solid. The yields for the preparation were similar and the analytical data ($^1$H NMR and MS) were identical.

15.ii. 6-((S)-5-{2-[((RS)-8-methoxy-1,2-dihydro-3-oxa-5,9-diaza-cyclopenta[a]naphthalen-1-ylmethyl)-amino]-ethyl}-2-oxo-oxazolidin-3-yl)-4H-benzo[1,4]thiazin-3-one Starting from intermediates 14.vi (20 mg) and 15.i (32 mg) and using procedure E, the title compound was obtained as a light yellow foam (12 mg, 27% yield).
MS (ESI, m/z): 508.0 [M+H$^+$].

Example 16

(S)-3-(2,3-dihydro-benzo[1,4]dioxin-6-yl)-2-oxo-oxazolidine-5-carboxylic acid [2-((RS)-8-methoxy-1,2-dihydro-3-oxa-5,9-diaza-cyclopenta[a]naphthalen-1-yl)-ethyl]-amide T3P® (114 mg; 0.11 mL; 50% in EA) was added at 0° C. to a solution of (5S)-3-(2,3-dihydro-1,4-benzodioxin-6-yl)-2-oxo-5-oxazolidinecarboxylic acid (43 mg; prepared according to WO 2008/126024), intermediate 9.iii (40 mg) and DIPEA (56 µL) in DMF (1 mL). The mixture was allowed to reach rt and was further stirred at rt temperature for 2 h. Water was added and the mixture was twice extracted with EA. The org. layers were washed with water and aq. citric acid (10%). The aq. layer was basified with NaHCO$_3$ and extracted with EA. The combined org. layers were washed with brine, dried over MgSO$_4$ and concentrated in vacuo. The product was purified by CC (DCM/MeOH/NH$_4$OH 1000:50:4), affording a light yellow foam (10 mg; 12% yield).
MS (ESI, m/z): 492.9 [M+H$^+$].

Example 17

6-((R)-5-{[((RS)-8-methoxy-1,2-dihydro-3-oxa-5,9-diaza-cyclopenta[a]naphthalen-2-ylmethyl)-amino]-methyl}-2-oxo-oxazolidin-3-yl)-4H-benzo[1,4]thiazin-3-one

17.i. 8-allyl-7-chloro-2-methoxy-[1,5]naphthyridine

A flask charged with trifluoromethanesulfonic acid 3-chloro-6-methoxy-[1,5]naphthyridin-4-yl ester (1.50 g; prepared according to WO 2004/058144), allyltributylstannane (1.68 g) and DMF was degassed with N$_2$. The reaction mixture was treated with LiCl (695 mg) and Pd(PPh$_3$)$_4$ (126 mg) and further stirred at 100° C. for 4 h. After cooling, the mixture was poured into 10% aq. NH$_4$OH and EA, the aq. layer was extracted with EA and the combined org. layers were washed with water (2×) and brine, dried over MgSO$_4$ and concentrated. The residue was purified by CC (Hept/EA 4:1), affording a yellow oil (795 mg; 77% yield).
MS (ESI, m/z): 235.1 [M+H$^+$].

17.ii. rac-3-(3-chloro-6-methoxy-[1,5]naphthyridin-4-yl)-propane-1,2-diol

A solution of intermediate 17.i (790 mg) in DCM (12 mL) was treated with water (1.7 mL), NMO (500 mg) and K$_2$OsO$_4$.2H$_2$O (12 mg). The resulting mixture was vigorously stirred at rt overnight. The phases were separated, the aq. layer was extracted several times with DCM/MeOH (9:1) and the combined org. layers were washed with aq. Na$_2$S$_2$O$_3$ (10%). The residue was by CC (DCM/MeOH/NH$_4$OH; 1000:50:4), affording a beige solid (674 mg; 75% yield).
MS (ESI, m/z): 269.2 [M+H$^+$].

17.iii. rac-1-(tert-butyl-dimethyl-silanyloxy)-3-(3-chloro-6-methoxy-[1,5]naphthyridin-4-yl)-propan-2-ol A solution of intermediate 17.ii (670 mg) in DCM (1 mL) was treated with imidazole (171 mg), DMAP (30 mg) and TBDMSCl (396 mg). The mixture was stirred at rt for 4 days. Water was added and the mixture was extracted with DCM. The org. layer was dried over MgSO$_4$ concentrated under reduced pressure and purified by CC (DCM/MeOH/NH$_4$OH; 1000:25:2 to 1000:100:8), affording a light yellow oil (533 mg; 56% yield).
MS (ESI, m/z): 383.1 [M+H$^+$].

17. iv. rac-2-(tert-butyl-dimethyl-silanyloxymethyl)-8-methoxy-1,2-dihydro-3-oxa-5,9-diaza-cyclopenta[a]naphthalene A suspension of intermediate 17.iii (530 mg), Cs$_2$CO$_3$ (676 mg), Pd(OAc)$_2$ (31 mg) and rac-2-(di-tert-butylphosphino)-1,1'-binaphthyl (66 mg) in toluene (3 mL) was heated to 70° C. under N$_2$ for 4 h. The reaction mixture was partitioned between water and EA and the org. layer was washed with brine, dried over Na$_2$SO$_4$, filtered and concentrated to dryness. The residue was purified by CC (EA/Hept 1:1), affording a brown oil (390 mg; 81% yield). MS (ESI, m/z): 347.1 [M+H$^+$].

17.v. rac-(8-methoxy-1,2-dihydro-3-oxa-5,9-diaza-cyclopenta[a]naphthalen-2-yl)-methanol A solution of intermediate 17.iv (390 mg) in THF (15 mL) was treated with a TBAF solution (1M in THF; 1.13 mL). The solution was stirred at rt overnight, partitioned between water and DCM. The org. layer was concentrated under reduced pressure and purified by CC (EA/Hept 1:2 to 2:1), affording a yellow solid (226 mg; 86% yield).

MS (ESI, m/z): 233.4 [M+H⁺].

17.vi. rac-C-(8-methoxy-1,2-dihydro-3-oxa-5,9-diaza-cyclopenta[a]naphthalen-2-yl)-methylamine DIAD (0.31 mL) was added at 0° C. to a solution of PPh₃ in THF (7 mL). After stirring for 15 min at 0° C., a solution of intermediate 17.v (226 mg) in THF (4 mL) was added dropwise, followed by DPPA (0.32 mL). The reaction mixture was allowed to reach rt and further stirred for 4 h. The mixture was concentrated under reduced pressure and the residue was purified by CC (EA) affording the intermediate rac-2-azidomethyl-8-methoxy-1,2-dihydro-3-oxa-5,9-diaza-cyclopenta[a]naphthalene as a yellow oil (870 mg).

MS (ESI, m/z): 258.2 [M+H⁺].

A solution of this intermediate azide in THF (10 mL) was treated with PPh₃ (514 mg) and water (0.18 mL). The mixture was heated at 50° C. for 1 h. The reaction mixture was concentrated and the residue was taken in DCM and extracted with 10% citric acid (2×). The combined aq. layers were basified with NH₄OH and then extracted with DCM/MeOH (9:1). The combined org. phases were dried over MgSO₄, concentrated under reduced pressure and purified by CC (DCM/MeOH/NH₄OH 1000:50:4 to 1000:100:8), affording the title compound as a light yellow solid (88 mg; 39% yield).

MS (ESI, m/z): 232.4 [M+H⁺].

17. vii. 6-((R)-5-{[((RS)-8-methoxy-1,2-dihydro-3-oxa-5,9-diaza-cyclopenta[a]naphthalen-2-ylmethyl)-amino]-methyl}-2-oxo-oxazolidin-3-yl)-4H-benzo[1,4]thiazin-3-one Starting from intermediates 17.vi (28 mg) and 1.vii (52 mg) and using procedure D, the title compound was obtained as a light yellow foam (15 mg, 24% yield).

MS (ESI, m/z): 494.2 [M+H⁺].

Example 18

6-((R)-5-{2-[((RS)-8-methoxy-1,2-dihydro-3-oxa-5,9-diaza-cyclopenta[a]naphthalen-2-ylmethyl)-amino]-ethyl}-2-oxo-oxazolidin-3-yl)-4H-benzo[1,4]oxazin-3-one 18.i. (2R)-tert-butyl-dimethyl-(2-oxiranyl-ethoxy)-silane and (2S)-4-(tert-butyl-dimethyl-silanyloxy)-butane-1,2-diol The title intermediates were prepared in analogy to Kishi et al., *Org. Lett.* (2005), 7, 3997, (intermediate S2-3) via hydrolytic kinetic resolution of (RS)-tert-butyl-dimethyl-(2-oxiranyl-ethoxy)-silane (prepared according to *J. Org. Chem.* (2008), 73, 1093). Two compounds were isolated after CC (Hept/EA 2:1).

First eluting compound: (2R)-tert-butyl-dimethyl-(2-oxiranyl-ethoxy)-silane (colourless oil, 25.3 g, 48% yield):

¹H NMR (CDCl₃) δ: 3.77 (t, J=6.4 Hz, 2H), 3.04 (m, 1H), 2.78 (m, 1H), 2.51 (dd, J=5.0, 2.9 Hz, 1H), 1.74 (m, 2H), 0.90 (d, J=0.6 Hz, 9H), 0.06 (s, 6H).

Second eluting compound: (2S)-4-(tert-butyl-dimethyl-silanyloxy)-butane-1,2-diol (colourless oil, 24.9 g, 43% yield):

¹H NMR (CDCl₃) δ: 3.89 (m, 3H), 3.62 (s, 1H), 3.53 (m, 1H), 3.42 (br. s, 1H), 2.29 (m, 1H), 1.70 (m, 2H), 0.90 (s, 9H), 0.09 (s, 6H).

18.ii. 6-[(R)-4-(tert-butyl-dimethyl-silanyloxy)-2-hydroxy-butylamino]-4H-benzo[1,4]oxazin-3-one A solution of 6-amino-4H-benzo[1,4]oxazin-3-one (commercial; 6.49 g, 39.5 mmol) and (2R)-tert-butyl-dimethyl-(2-oxiranyl-ethoxy)-silane (first eluting compound of step 18.i, 8.0 g, 39.5 mmol) in 9-1 EtOH/H₂O (240 mL) was heated at 80° C. for 2 days. The mixture was concentrated under reduced pressure. Residual starting aniline could be removed by addition of Et₂O/MeOH followed by filtration. The filtrate was concentrated under reduced pressure and the residue was purified by CC (DCM/MeOH/NH₄OH 1000:50:4) to afford the title intermediate as a brown oil (5.82 g, 40% yield).

MS (ESI, m/z): 367.3 [M+H⁺].

18.iii. 6-{(R)-5-[2-(tert-butyl-dimethyl-silanyloxy)-ethyl]-2-oxo-oxazolidin-3-yl}-4H-benzo[1,4]oxazin-3-one A solution of intermediate 18.ii (5.8 g, 15.8 mmol) and CDI (3.07 g, 1.2 eq.) in THF (50 mL) was heated at 50° C. overnight. The mixture was concentrated under reduced pressure and partitioned between EA and water. The aq. layer was extracted once more with EA and the combined org. layers were dried over MgSO₄ and concentrated. The residue was triturated with Et₂O/EA/MeOH to afford the title compound as a beige solid (2.7 g, 43% yield).

MS (ESI, m/z): 393.5 [M+H⁺].

18.iv. 6-[(R)-5-(2-hydroxy-ethyl)-2-oxo-oxazolidin-3-yl]-4H-benzo[1,4]oxazin-3-one A solution of intermediate 18.iii (2.70 g, 6.88 mmol) in THF (15 mL) was treated with TBAF (1M solution in THF, 8.3 mL, 1.2 eq.) at 0° C. The solution was stirred at 0° C. for 2 h. The mixture was partitioned between water and EA and the aq. phase was extracted with EA (3×). The combined org. layers were washed with water and brine, dried over MgSO₄ and concentrated. The residue was triturated with Et₂O/MeOH to afford the title compound as an off-white solid (1.25 g, 65% yield).

MS (ESI, m/z): 279.5 [M+H⁺].

18.v. Methanesulfonic acid 2-[(R)-2-oxo-3-(3-oxo-3,4-dihydro-2H-benzo[1,4]oxazin-6-yl)-oxazolidin-5-yl]-ethyl ester A solution of intermediate 18.iv (2.1 g, 7.55 mmol) and DIPEA (3.57 mL, 2.9 eq.) in anhydrous DCM (40 mL) was cooled to 0° C. and treated dropwise with MsCl (0.71 mL, 1.2 eq.). The resulting mixture was stirred at 0° C. for 1 h. Water and DCM were added and the phases separated. The org. layer was dried over MgSO₄ and concentrated under reduced pressure. The residue was triturated with MeOH to afford the title compound as an off-white solid (1.16 g, 43% yield).

¹H NMR (DMSO-d6) δ: 10.72 (s, 1H), 7.30 (d, J=2.1 Hz, 1H), 6.93 (m, 2H), 4.76 (m, 1H), 4.52 (s, 2H), 4.34 (m, 2H), 4.11 (t, J=8.8 Hz, 1H), 3.72 (m, 1H), 3.20 (s, 3H), 2.17 (m, 2H).

MS (ESI, m/z): 357.2 [M+H⁺].

18. vi. 6-[(R)-5-(2-iodo-ethyl)-2-oxo-oxazolidin-3-yl]-4H-benzo[1,4]oxazin-3-one A suspension of intermediate 18.v (1.16 g, 3.26 mmol) and NaI (1.46 g, 3 eq.) in 2-butanone (10 mL) was heated at 85° C.

overnight. After cooling, the mixture was diluted with ether/EA (10 mL) and treated with 10% aq. Na$_2$S$_2$O$_3$ (30 mL). After stirring for 10 min the phases were separated and the aq. layer was washed with EA. The combined org. layers were washed with water (2×), dried over MgSO$_4$ and concentrated under reduced pressure to afford the title compound as an off-white solid (0.91 g, 72% yield).

$^1$H NMR (CDCl$_3$) δ: 8.24 (s, 1H), 7.42 (d, J=2.3 Hz, 1H), 6.95 (d, J=8.8 Hz, 1H), 6.79 (dd, J=8.8, 2.6 Hz, 1H), 4.80 (m, 1H), 4.59 (s, 2H), 4.14 (t, J=8.8 Hz, 1H), 3.65 (dd, J=8.8, 6.7 Hz, 1H), 3.33 (m, 2H), 2.30 (m, 2H).

18.vii. 6-((R)-5-{2-[((RS)-8-methoxy-1,2-dihydro-3-oxa-5,9-diaza-cyclopenta[a]naphthalen-2-ylmethyl)-amino]-ethyl}-2-oxo-oxazolidin-3-yl)-4H-benzo[1,4]oxazin-3-one Starting from intermediates 17.vi (28 mg) and 18.vi (49 mg) and using procedure D, the title compound was obtained as a light brown foam (27 mg, 43% yield).

$^1$H NMR (CDCl$_3$) δ: 8.41 (d, J=2.3 Hz, 1H), 8.12 (m, 1H), 7.27 (m, 1H), 6.91 (m, 2H), 6.79 (m, 1H), 5.18 (m, 1H), 4.75 (m, 1H), 4.56 (s, 2H), 4.03 (s, 3H), 3.90 (m, 1H) 3.62 (m, 2H), 3.32 (m, 2H), 2.95 (m, 4H), 2.04 (m, 1H), 1.91 (m, 1H).

MS (ESI, m/z): 492.2 [M+H$^+$].

Example 19

6-((R)-5-{2-[((RS)-8-methoxy-1,2-dihydro-3-oxa-5,9-diaza-cyclopenta[a]naphthalen-2-ylmethyl)-amino]-ethyl}-2-oxo-oxazolidin-3-yl)-4H-benzo[1,4]thiazin-3-one Starting from intermediates 17.vi (30 mg) and 13.iv (51 mg) and using procedure E, the title compound was obtained as a light yellow foam (19 mg, 27% yield).

MS (ESI, m/z): 508.0 [M+H$^+$].

Example 20

(RS)-3-(2,3-dihydro-benzo[1,4]dioxin-6-yl)-5-{[2-((R)-8-methoxy-1,2-dihydro-3-oxa-5,9-diaza-cyclopenta[a]naphthalen-1-yl)-ethylamino]-methyl}-oxazolidin-2-one Starting from intermediate 9.iii (40 mg) and (5S)-3-(2,3-dihydro-1,4-benzodioxin-6-yl)-5-[[(methylsulfonyl)oxy]methyl]-2-oxazolidinone (54 mg; prepared according to WO 2008/126034) and using procedure E, the title compound was obtained as a light yellow foam (6 mg, 8% yield).

$^1$H NMR (CDCl$_3$) δ: 8.46 (d, J=4.7 Hz, 1H), 8.09 (d, J=8.8 Hz, 1H), 7.10 (dd, J=4.4, 2.6 Hz, 1H), 7.00 (m, 1H), 6.88 (m, 2H), 5.11 (m, 1H), 4.90 (m, 1H), 4.25 (m, 4H), 4.16 (m, 1H), 4.05 (s, 3H), 3.78 (m, 1H), 3.70-2.75 (m, 6H), 2.52 (m, 2H).

MS (ESI, m/z): 479.1 [M+H$^+$].

Pharmacological Properties of the Invention Compounds
In Vitro Assays
Experimental Methods:

Minimal inhibitory concentrations (MICs; mg/l) were determined in cation-adjusted Mueller-Hinton Broth by a microdilution method following the description given in "Methods for Dilution Antimicrobial Susceptibility Tests for Bacteria that Grow Aerobically", Approved standard, 7th ed., Clinical and Laboratory Standards Institute (CLSI) Document M7-A7, Wayne, Pa., USA, 2006.

Results:
All Example compounds were tested against several Gram positive and Gram negative bacteria such as *S. aureus, E. faecalis, S. pneumoniae, M catarrhalis, A. baumanii, E. coli* or *P. aeruginosa.*

Typical antibacterial test results are given in the table hereafter (MIC in mg/l).

| Example No. | MIC for S. aureus A798 | Example No | MIC for S. aureus A798 |
|---|---|---|---|
| 1 | ≦0.031 | 2 | ≦0.031 |
| 3 | ≦0.031 | 4 | ≦0.031 |
| 5 | ≦0.031 | 6 | ≦0.031 |
| 7 | ≦0.031 | 8 | ≦0.031 |
| 9 | ≦0.031 | 10 | ≦0.031 |
| 11 | 0.25 | 12 | ≦0.031 |
| 13 | ≦0.031 | 14 | ≦0.031 |
| 15 | ≦0.031 | 16 | ≦0.031 |
| 17 | ≦0.031 | 18 | ≦0.031 |
| 19 | ≦0.031 | 20 | 1 |

The invention claimed is:
1. A compound of formula I wherein
R$^1$ is alkoxy or halogen;
W is CH or N;
A is O or NH;
B is CO or (CH$_2$)$_q$;
G is one of:

wherein Q represents O or S, Z represents CH or N, R$^2$ represents halogen and R$^3$ represents alkyl;
m is 0 or 1;
n is 1 or 2;
p is 0 or 1, provided m and p are not each 0; and
q is 1 or 2;
or a salt of the compound.

2. The compound according to claim 1, wherein R$^1$ is alkoxy;

W is CH or N;
A is O or NH;
B is CO or $(CH_2)_q$;
G is one of:

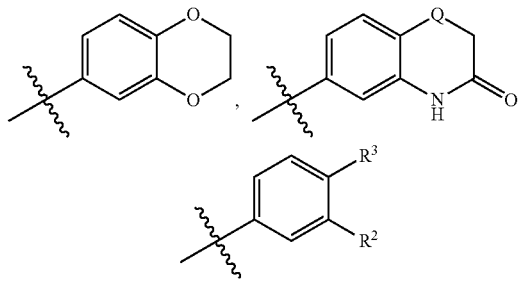

wherein Q represents O or S, $R^2$ represents halogen and $R^3$ represents alkyl;
m is 0 and n is 1 or 2 or m is 1 and n is 1;
p is 0 or 1, provided m and p are not each 0; and
q is 1 or 2;
or a salt of the compound.

3. The compound according to claim 1,
wherein
$R^1$ is alkoxy or halogen;
W is CH or N;
A is O or NH;
G is one of:

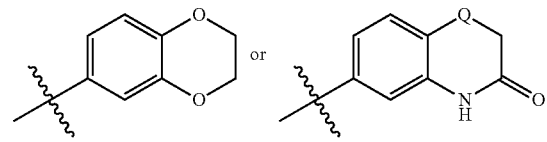

wherein Q represents O or S;
m is 0 or 1; and
n is 1 or 2;
or a salt of the compound.

4. The compound according to claim 1, wherein $R^1$ is methoxy;
or a salt of the compound.

5. The compound according to claim 1, wherein W is CH; or a salt of the compound.

6. The compound according to claim 1, wherein W is N; or a salt of the compound.

7. The compound according to claim 1, wherein A is O; or a salt of the compound.

8. The compound according to claim 7, wherein p is 1; or a salt of the compound.

9. The compound according to claim 1, wherein A is NH; or a salt of the compound.

10. The compound according to claim 1, wherein G is:

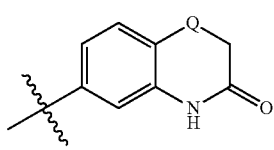

wherein Q represents O or S;
or a salt of the compound.

11. The compound according to claim 1, wherein the compound is:
6-((R)-5-{[(6-methoxy-3,4-dihydro-2H-1-oxa-5-aza-phenanthren-3-ylmethyl)-amino]-methyl}-2-oxo-oxazolidin-3-yl)-4H-benzo[1,4]thiazin-3-one;
6-((R)-5-{[(6-methoxy-3,4-dihydro-2H-1-oxa-5-aza-phenanthren-3-ylmethyl)-amino]-methyl}-2-oxo-oxazolidin-3-yl)-4H-benzo[1,4]oxazin-3-one;
6-((R)-5-{[(6-methoxy-3,4-dihydro-2H-1-oxa-5,9-diaza-phenanthren-3-ylmethyl)-amino]-methyl}-2-oxo-oxazolidin-3-yl)-4H-benzo[1,4]oxazin-3-one;
6-((R)-5-{[(6-methoxy-3,4-dihydro-2H-1-oxa-5,9-diaza-phenanthren-3-ylmethyl)-amino]-methyl}-2-oxo-oxazolidin-3-yl)-4H-benzo[1,4]thiazin-3-one;
6-((R)-5-{[(6-methoxy-1,2,3,4-tetrahydro-1,5,9-triaza-phenanthren-3-ylmethyl)-amino]-methyl}-2-oxo-oxazolidin-3-yl)-4H-benzo[1,4]thiazin-3-one;
6-((R)-5-{[2-(2-methoxy-8,9-dihydro-furo[2,3-h]quinolin-9-yl)-ethylamino]-methyl}-2-oxo-oxazolidin-3-yl)-4H-benzo[1,4]thiazin-3-one;
6-((R)-5-{[2-(2-methoxy-8,9-dihydro-furo[2,3-h]quinolin-9-yl)-ethylamino]-methyl}-2-oxo-oxazolidin-3-yl)-4H-benzo[1,4]oxazin-3-one;
6-((R)-5-{[(2-methoxy-8,9-dihydro-furo[2,3-h]quinolin-9-ylmethyl)-amino]-methyl}-2-oxo-oxazolidin-3-yl)-4H-benzo[1,4]thiazin-3-one;
6-((R)-5-{[2-(8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]thiazin-3-one;
6-((R)-5-{[2-(8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]oxazin-3-one;
(R)-3-(3-fluoro-4-methyl-phenyl)-5-{[2-(8-methoxy-1,2-dihydro-3-oxa-5,9-diaza-cyclopenta[a]naphthalen-1-yl)-ethylamino]-methyl}-oxazolidin-2-one;
6-((S)-5-{[2-(8-methoxy-1,2-dihydro-3-oxa-5,9-diaza-cyclopenta[a]naphthalen-1-yl)-ethylamino]-methyl}-2-oxo-oxazolidin-3-yl)-4H-benzo[1,4]thiazin-3-one;
6-((R)-5-{2-[2-(8-methoxy-1,2-dihydro-3-oxa-5,9-diaza-cyclopenta[a]naphthalen-1-yl)-ethylamino]-ethyl}-2-oxo-oxazolidin-3-yl)-4H-benzo[1,4]thiazin-3-one;
6-((R)-5-{2-[(8-methoxy-1,2-dihydro-3-oxa-5,9-diaza-cyclopenta[a]naphthalen-1-ylmethyl)-amino]ethyl}-2-oxo-oxazolidin-3-yl)-4H-benzo[1,4]thiazin-3-one;
6-((S)-5-{2-[(8-methoxy-1,2-dihydro-3-oxa-5,9-diaza-cyclopenta[a]naphthalen-1-ylmethyl)-amino]-ethyl}-2-oxo-oxazolidin-3-yl)-4H-benzo[1,4]thiazin-3-one;
(S)-3-(2,3-dihydro-benzo[1,4]dioxin-6-yl)-2-oxo-oxazolidine-5-carboxylic acid [2-(8-methoxy-1,2-dihydro-3-oxa-5,9-diaza-cyclopenta[a]naphthalen-1-yl)-ethyl]-amide;
6-((R)-5-{[(8-methoxy-1,2-dihydro-3-oxa-5,9-diaza-cyclopenta[a]naphthalen-2-ylmethyl)-amino]-methyl}-2-oxo-oxazolidin-3-yl)-4H-benzo[1,4]thiazin-3-one;
6-((R)-5-{2-[(8-methoxy-1,2-dihydro-3-oxa-5,9-diaza-cyclopenta[a]naphthalen-2-ylmethyl)-amino]-ethyl}-2-oxo-oxazolidin-3-yl)-4H-benzo[1,4]oxazin-3-one;
6-((R)-5-{2-[(8-methoxy-1,2-dihydro-3-oxa-5,9-diaza-cyclopenta[a]naphthalen-2-ylmethyl)-amino]-ethyl}-2-oxo-oxazolidin-3-yl)-4H-benzo[1,4]thiazin-3-one;
3-(2,3-dihydro-benzo[1,4]dioxin-6-yl)-5-{[2-((R)-8-methoxy-1,2-dihydro-3-oxa-5,9-diaza-cyclopenta[a]naphthalen-1-yl)-ethylamino]-methyl}-oxazolidin-2-one;
or a salt of the compound.

12. A medicament comprising the compound of claim 1, or a pharmaceutically acceptable salt thereof.

13. A pharmaceutical composition comprising, as an active principle, the compound of claim 1, or a pharmaceutically acceptable salt thereof, and at least one therapeutically inert excipient.

14. A method for the prevention or treatment of bacterial infection comprising the administration of the compound of claim 1, or of a pharmaceutically acceptable salt thereof.

15. A method for the prevention or treatment of bacterial infection comprising the administration of the compound of claim 1, or a pharmaceutically acceptable salt thereof, to a patient in need thereof.

* * * * *

UNITED STATES PATENT AND TRADEMARK OFFICE
CERTIFICATE OF CORRECTION

PATENT NO. : 8,466,168 B2  
APPLICATION NO. : 13/057650  
DATED : June 18, 2013  
INVENTOR(S) : Hubschwerlen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 321 days.

Signed and Sealed this
Eighth Day of September, 2015

Michelle K. Lee
*Director of the United States Patent and Trademark Office*